United States Patent [19]
Briles et al.

[11] Patent Number: 5,753,463
[45] Date of Patent: May 19, 1998

[54] STRUCTURAL GENE OF PNEUMOCOCCAL PROTEIN

[75] Inventors: David E. Briles; Janet L. Yother, both of Birmingham, Ala.

[73] Assignee: UAB Research Foundation, Birmingham, Ala.

[21] Appl. No.: 469,434

[22] Filed: Jun. 6, 1995

Related U.S. Application Data

[60] Continuation of Ser. No. 72,065, Jun. 3, 1993, abandoned, which is a division of Ser. No. 835,698, Feb. 12, 1992, abandoned, which is a continuation-in-part of Ser. No. 656,773, Feb. 15, 1991, abandoned.

[51] Int. Cl.$^6$ .............................. C12P 21/02; C12N 1/21; C12N 15/31; C07K 1/18
[52] U.S. Cl. ............... 435/69.3; 435/252.3; 435/252.33; 435/253.1; 435/253.4; 435/849; 435/885; 530/416; 530/417; 536/23.7
[58] Field of Search ........................... 435/69.3, 252.33, 435/252.3, 253.4, 320.1, 844, 885, 253.1; 536/23.7; 530/416, 417

[56] References Cited

U.S. PATENT DOCUMENTS 4,496,538 1/1985 Gordon .
4,673,574 6/1987 Anderson .

OTHER PUBLICATIONS

McDaniel et al (I), J.Exp.Med. 160:386–397, 1984.
McDaniel et al (II), Microbial Pathogenesis 1:519–531, 1986.
McDaniel et al (III), J.Exp.Med. 165:381–394, 1987.
McDaniel et al (IV), Infect. Immun., 59:222–228, 1991.
Crain et al, Infect. Immun., 58:3293–3299, 1990.
Abstracts of 90th Annual Meeting of the American Society for Microbiology, p. 98, item D–106, May 1990.
Abstracts of 3rd International ASM Conference on Streptococcal Genetics, p. 11, item 12, Jun. 1990.
Talkington et al, Infect. Immun. 59:1285–1289, 1991.
Yother et al, J. Bacteriol. 174:601–609, 1992; and Yother et al, J. Bacteriol. 174:610–618, 1992.
Growth Characterisitcs of Group A Streptococci in a New Chemically Defined Medium, Rijn et al—Inf. and Imm. Feb. 1980, pp. 444–448.
Young and Davis PNAS 80:1194–98 Mar. 1983.
McDaniel et al 1989 89th ASM See Abstract D–255.
Dertzbaugh et al Gene 82 332–342 1989.
Stover et al nature 351:456–606/91.

Primary Examiner—Anthony C. Caputa
Attorney, Agent, or Firm—Curtis Morris & Safford, P.C.

[57] ABSTRACT

A purified pneumococcal surface protein A (PspA) comprises a truncated form of the PspA protein which is immunoprotective and contains the protective epitopes of PspA. The PspA protein is soluble in physiologic solution and lacks at least the cell membrane anchor region of the whole protein. The protein is formed by insertion-duplication of mutagenesis of *S. pneumoniae* with pspA gene and expression of the truncated protein into the growth medium.

7 Claims, 8 Drawing Sheets

| | | | | a | b | c | d | e | f | g | |
|---|---|---|---|---|---|---|---|---|---|---|---|
| GLU | GLU | ser | pro | val | ala | ser | gln | ser | LYS | ala | GLU | LYS | ASP | 14 |
| | | | | | | | tyr | ASP | ala | ala | LYS | LYS | ASP | 21 |
| | | | | | | | ala | LYS | asn | ala | LYS | LYS | ala | 28 |
| | | | | | | | val | GLU | ASP | ala | gln | LYS | ala | 35 |
| | | | | | | | leu | ASP | ASP | ala | LYS | ala | ala | 42 |
| | | | | | | | gln | LYS | LYS | | | | | 45 |

FIG. 3a

```
pspa - sequence -> 1-phase Translation
DNA and derived amino acid 2086 b.p.  AAGCTTATGATA.....TCTTTAGGTACC  linear 1
AAG CCT ATG ATA TAG AAA TTT GTA ACA AAA CTT TAA TAT AAA TAT TTA
 61
CGG AGG AGG CTT ATA CTT AAT ATA AGT ATA TGA AAA TGA CTA TCA GAA AAG AGG TAA
121
ATT TAG ATG AAT AAG AAA ATG ATT TTA ACA AGT CTA GCC AGC GTC GCT ATC TTA GGG
        met asn lys lys met ile leu thr ser leu ala ser val ala ile leu gly
181
GCT GGT TTT GTT GTT CCT CAG CCT GTT GTA GCC AGA GCA GAA GAA GCC CCC GTA GCC AGT
ala gly phe val val pro gln pro val val ala arg ala glu glu ala pro val ala ser
241
CAG TCT AAA GCT GAG GCT TAT GAC GCA GCA GAA GCT GAA CTA GCT GCT GCT AAA AAA
gln ser lys ala glu ala tyr asp ala ala glu ala glu leu ala ala ala lys lys
301
GCA AAA GAG GCT GAG AAG CAA CAA GCT GAA GAT CTA TTA GCT GCT GCA CAA GCT TAT
ala lys glu ala glu lys gln gln ala glu asp leu leu ala ala ala gln ala tyr
361
GCA GTA GAT CAG ACT AAG GCA GAG ATA GCC GCC TAT CTA GAA AAG CAA CAA GAA GCT
ala val asp gln thr lys ala glu ile ala ala tyr leu glu lys gln gln glu ala
421
GAG GAA AAG GCA GCA GCA GCT GAG AAG GTT AAG ATG ATA GCG GCG GCT GAA GAG CGC
glu glu lys ala ala ala ala glu lys val lys met ile ala ala ala glu glu arg
481
GAT AAG GTT GTG ACT GCA GCA AAA TAT CGA TAT TAT CCT CAG ACA ATG ATA TAT TAT
asp lys val val thr ala ala lys tyr arg tyr tyr pro gln thr met ile tyr tyr
541
GCC GCA GAC GAT GAT GAT GCA GCA AAT ATG GCA GCG AAG ACT CCT CCA GAG GAG GCT
ala ala asp asp asp asp ala ala asn met ala ala lys thr pro pro glu glu ala
601
AAA ACT TTT AAT AAT GCA CGA ATG AAA CAA GTT GCA CCA CCA GAG GAG TTG AAA CAC
lys thr phe asn asn ala arg met lys gln val ala pro pro glu glu leu lys asp
661
ACT AAG AAA TCA GAA GCT GCT GCG GCT AAA CAA AAA GAG GAA CTT CTA AAA GCA GAG
thr lys lys ser glu ala ala ala ala lys gln lys glu glu leu leu lys ala glu
```

| # | 1 | 2 | 3 | 4 | 5 | 6 | 7 | 8 | 9 | 10 | # | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 1381 | TCA ser | ATG met | GCG ala | ACA thr | GGA gly | TGG trp | CTC leu | CAA gln | AAC asn | AAC asn | 1411 | GGT gly | TCA ser | TGG trp | TAC tyr | TAC tyr | CTC leu | AAC asn | AGC ser | AAT asn | GGT gly |
| 1441 | GCT ala | ATG met | GCT ala | ACA thr | GGT gly | TGG trp | CTC leu | CAA gln | AAC asn | AAT asn | 1471 | GGT gly | TCA ser | TGG trp | TAC tyr | TAT tyr | CTC leu | AAC asn | GCT ala | AAC asn | GGC gly |
| 1501 | GCT ala | ATG met | GCA ala | ACA thr | GGT gly | TGG trp | GCT ala | AAA lys | TAC tyr | AAC asn | 1531 | GGT gly | TCA ser | TGG trp | TAC tyr | TAC tyr | CTC leu | AAC asn | GCT ala | AAT asn | GGT gly |
| 1561 | GCT ala | ATG met | GCT ala | ACA thr | GGT gly | TGG trp | CTC leu | CAA gln | TAC tyr | AAC asn | 1591 | GGT gly | TCA ser | TGG trp | TAC tyr | TAC tyr | CTC leu | AAC asn | GCT ala | AAC asn | GGC gly |
| 1621 | GCT ala | ATG met | GCT ala | ACA thr | GGT gly | TGG trp | GCT ala | AAA lys | GTC val | AAC asn | 1651 | GGT gly | TCA ser | TGG trp | TAC tyr | TAT tyr | CTC leu | AAC asn | GCT ala | AAT asn | GGT gly |
| 1681 | GCT ala | ATG met | GCT ala | ACA thr | GGT gly | TGG trp | CTC leu | CAA gln | TAC tyr | AAC asn | 1711 | GGT gly | TCA ser | TGG trp | TAC tyr | TAC tyr | CTC leu | AAC asn | GCT ala | AAC asn | GGC gly |
| 1741 | GCT ala | ATG met | GCA ala | ACA thr | GGT gly | TGG trp | GCT ala | AAA lys | GTC val | AAC asn | 1771 | GGT gly | TCA ser | TGG trp | TAC tyr | TAC tyr | CTC leu | AAC asn | GCT ala | AAT asn | GGT gly |
| 1801 | GCT ala | ATG met | GCA ala | ACA thr | GGT gly | TGG trp | GTG val | AAA lys | TAC tyr | AAC asn | 1831 | GGT gly | TCA ser | TGG trp | TAC tyr | TAC tyr | CTT leu | AAC asn | GCA ala | AAT asn | GGT gly |
| 1861 | GCT ala | ATG met | GCT ala | GCA ala | AGC ser | CAA gln | TGG trp | TTC phe | GAT asp | GGA gly | 1891 | GAT asp | ACC ser | AAA lys | TGG trp | CTT leu | GAA glu | GCA ala | AAT asn | GGT gly | TTA leu |
| 1921 | GCT ala | GCC ala | AAA lys | CTT leu | AAC asn | ATT ile | ACA thr | TTC phe | AAA lys | ATG met | 1951 | TCA ser | GAT asp | TAT tyr | GTC val | AAA lys | TAT tyr | AAT asn | AAT asn | GAA glu | TGG trp |
| 1981 | GCT ala | GGT gly | CTT leu | GCC ala | GAT asp | GTC val | ACA thr | GCA ala | TTT phe | TGT cys | 2011 | GGC gly | TCA ser | AAA lys | TGG trp | GTC val | ACA thr | AAA lys | TCA ser | GGT gly | TGG trp |
| 2041 | GTT val | TAA OCH | GCC ala | GAT asp | TAA OCH | TTG leu | ACA thr | AAA lys | TTC phe | ATG met | 2071 | GTA val | TGA OPA | GAA glu | AAC asn | AAC asn | TCA ser | TAT tyr | AGG tyr | AGG tyr | AAA lys |
| | GAT asp | AAG lys | CTT val | CGA arg | TTG leu | AGA arg | TTT phe | ATG met | TAC tyr | TTC phe | | GTA val | TGA OPA | | | TAC tyr | GCC ala | TAA OCH | TTT phe | TAC tyr | |

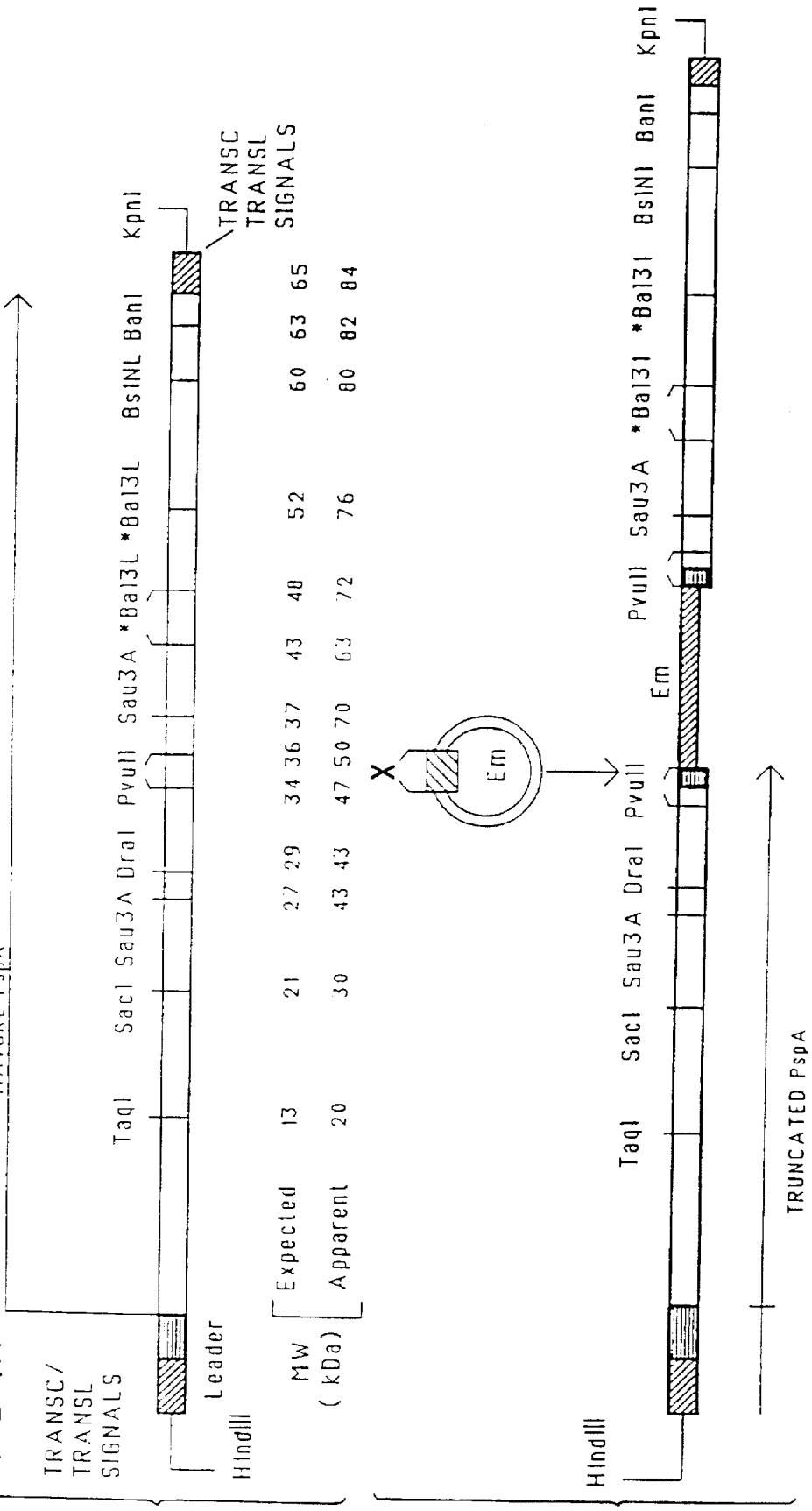

Location of epitopes detected by monoclonal antibodies to PspA

|  |  |  | a | b | c | d | e | f | g |
|---|---|---|---|---|---|---|---|---|---|
|  |  | 1 | E | E | s | p | y | a | s |
|  |  | 8 | Q | s |  |  |  |  |  |
|  |  |  |  |  | K | a | E | K | D |
|  |  | 15 | y | D | a | a | K | K | D |
|  |  | 22 | a | K | N | a | K | K | a |
|  |  | 29 | y | E | D | a | Q | K | a |
|  |  | 36 | L | D | D | a | K | a | a |
| XI1526* |  | 43 | Q | K | K | y | D | E | D |
| XI126* |  | 50 | Q | K | K | t | E | E | K |
| XIR35 |  | 57 | a | a | l | E | K | a | a |
| XIR148 |  | 64 | s | E | E | m | D | K | a |
| XIR1224 |  | 71 | v | a | a | v | Q | Q | a |
|  |  | 78 | y | l | a | y | Q | Q | a |
|  |  | 85 | t | D | K | a | a | K | D |
|  |  | 92 | a |  |  |  |  |  |  |
|  |  |  |  |  |  | a | D | K | m |
|  |  | 97 | l | D | E | a | K | K | R |
|  |  | 104 | E | E | E | a | K | t | K |
|  |  | 111 | l | N | t | v | R | a | m |
|  |  | 118 | v | v | p | E | p | E | Q |
|  |  | 125 | l | a | E | t | K | K | K |
|  | 138 HHHH | 132 | s | E | E | a | K | Q | K |
|  |  | 139 | a | p | E | l | t | K | K |
|  |  | 146 | l | E | E | a | K | a | K |
|  |  | 153 | l | E | E | a | E | K | K |
|  |  | 160 | a | t | E | a | K | Q | K |
| XIR16 |  | 167 | v | D |  |  |  |  |  |
|  |  |  |  |  | a | E | E | v | a |
|  |  | 174 | p | Q | a |  |  |  |  |
|  |  |  |  |  |  |  |  |  | K |
|  |  | 178 | l | a | E | l | E | N | Q |
|  |  | 185 | v | H | R | l | E | Q | E |
|  | 193 HHHH | 192 | l | K | E | l | D | E | s |
|  |  | 199 | E |  |  |  |  |  |  |
|  |  |  |  |  |  | s | E | D | y |
|  |  | 204 | a | K | E | g | l | R | a |
|  |  | 211 | p | L | Q | s | K | l | D |
| XI64* |  | 218 | a | K | K | a | K | l | s |
| XIR278* |  | 225 | K |  |  |  |  |  |  |
| XI1325* |  | 226 | l | E | E | l | s | D | K |
|  |  | 233 | l | D | E | l | D | a | E |
|  |  | 240 | l | a | K | l | E | D | Q |
|  |  | 247 | L | K | a | a | E | E | N |
|  |  | 254 |  | N | N | v | E | D | y |
|  | 261 HHHH | 260 | l | K | E | g | l | E | K |
|  |  | 267 | t | l | a | a | K | K | a |
| XI1323* |  | 274 | E |  |  |  |  |  |  |
|  |  | 275 | l | E | K | t | E | a | D |
|  |  | 282 | l | K | K | a | v | N | E |

FIG. 5

ANTIBODY REACTIVITY

| | Xi 126 | XiR 1224 | XiR 148 | XiR 1526 | XiR 35 | XiR 16 | XiR 278 | XiR 1325 | XiR 64 | XiR 1323 |
|---|---|---|---|---|---|---|---|---|---|---|
| KSD 1014 | ++ | ++ | ++ | ++ | ++ | ++ | ++ | ++ | ++ | ++ |
| JY 4306 | ++ | ++ | ++ | ++ | ++ | ++ | + | ++ | ++ | ++ |
| JY 4310 | ++ | + | ++ | ++ | ++ | ++ | – | – | – | – |
| JY 4285 | ++ | + | ++ | ++ | ++ | + | – | – | – | – |
| KSD 1500 | – | – | – | – | – | – | – | – | – | – |
| BC 100 | – | – | – | – | – | – | ++ | ++ | ++ | ++ |
| BC 207 | – | – | – | – | – | + | ++ | ++ | ++ | ++ |

FIG. 6

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2085 base pairs
        ( B ) TYPE: nucleic acid
        ( C ) STRANDEDNESS: double
        ( D ) TOPOLOGY: linear 5,753,463

15 16

-continued ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Streptococcus pneumoniae
    ( B ) STRAIN: Rx1

( v i i ) IMMEDIATE SOURCE:
    ( B ) CLONE: JY2008

( i x ) FEATURE:
    ( A ) NAME/KEY: intron
    ( B ) LOCATION: 1..2085

( i x ) FEATURE:
    ( A ) NAME/KEY: CDS
    ( B ) LOCATION: join(127..1983, 1987..1992, 1996..2007, 2011
        . . 2025, 2029..2031, 2035..2085)

( x i ) SEQUENCE DESCRIPTION: SEQ ID NO:1:

```
AAGCTTATGA TATAGAAATT TGTAACAAAA ATGTAATATA AAACACTTGA CAAATATTTA   60

CGGAGGAGGC TTATACTTAA TATAAGTATA GTCTGAAAAT GACTATCAGA AAAGAGGTAA  120

ATTTAG ATG AAT AAG AAA AAA ATG ATT TTA ACA AGT CTA GCC AGC GTC    168
       Met Asn Lys Lys Lys Met Ile Leu Thr Ser Leu Ala Ser Val
        1               5                  10

GCT ATC TTA GGG GCT GGT TTT GTT GCG TCT CAG CCT ACT GTT GTA AGA   216
Ala Ile Leu Gly Ala Gly Phe Val Ala Ser Gln Pro Thr Val Val Arg
 15              20                  25                  30

GCA GAA GAA TCT CCC GTA GCC AGT CAG TCT AAA GCT GAG AAA GAC TAT   264
Ala Glu Glu Ser Pro Val Ala Ser Gln Ser Lys Ala Glu Lys Asp Tyr
             35                  40                  45

GAT GCA GCG AAG AAA GAT GCT AAG AAT GCG AAA AAA GCA GTA GAA GAT   312
Asp Ala Ala Lys Lys Asp Ala Lys Asn Ala Lys Lys Ala Val Glu Asp
         50                  55                  60

GCT CAA AAG GCT TTA GAT GAT GCA AAA GCT GCT CAG AAA AAA TAT GAC   360
Ala Gln Lys Ala Leu Asp Asp Ala Lys Ala Ala Gln Lys Lys Tyr Asp
     65                  70                  75

GAG GAT CAG AAG AAA ACT GAG GAG AAA GCC GCG CTA GAA AAA GCA GCG   408
Glu Asp Gln Lys Lys Thr Glu Glu Lys Ala Ala Leu Glu Lys Ala Ala
 80                  85                  90

TCT GAA GAG ATG GAT AAG GCA GTG GCA GCA GTT CAA CAA GCG TAT CTA   456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG   504
Ala Tyr Gln Gln Ala Thr Asp Lys Ala Ala Lys Asp Ala Ala Asp Lys
             115                 120                 125

ATG ATA GAT GAA GCT AAG AAA CGC GAA GAA GAG GCA AAA ACT AAA TTT   552
Met Ile Asp Glu Ala Lys Lys Arg Glu Glu Glu Ala Lys Thr Lys Phe
         130                 135                 140

AAT ACT GTT CGA GCA ATG GTA GTT CCT GAG CCA GAG CAG TTG GCT GAG   600
Asn Thr Val Arg Ala Met Val Val Pro Glu Pro Glu Gln Leu Ala Glu
     145                 150                 155

ACT AAG AAA AAA TCA GAA GAA GCT AAA CAA AAA GCA CCA GAA CTT ACT   648
Thr Lys Lys Lys Ser Glu Glu Ala Lys Gln Lys Ala Pro Glu Leu Thr
 160                 165                 170

AAA AAA CTA GAA GAA GCT AAA GCA AAA TTA GAA GAG GCT GAG AAA AAA   696
Lys Lys Leu Glu Glu Ala Lys Ala Lys Leu Glu Glu Ala Glu Lys Lys
175                 180                 185                 190

GCT ACT GAA GCC AAA CAA AAA GTG GAT GCT GAA GAA GTC GCT CCT CAA   744
Ala Thr Glu Ala Lys Gln Lys Val Asp Ala Glu Glu Val Ala Pro Gln
             195                 200                 205
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| GCT | AAA | ATC | GCT | GAA | TTG | GAA | AAT | CAA | GTT | CAT | AGA | CTA | GAA | CAA | GAG | 792 |
| Ala | Lys | Ile | Ala | Glu | Leu | Glu | Asn | Gln | Val | His | Arg | Leu | Glu | Gln | Glu |     |
|     |     | 210 |     |     |     |     | 215 |     |     |     |     | 220 |     |     |     |     |
| CTC | AAA | GAG | ATT | GAT | GAG | TCT | GAA | TCA | GAA | GAT | TAT | GCT | AAA | GAA | GGT | 840 |
| Leu | Lys | Glu | Ile | Asp | Glu | Ser | Glu | Ser | Glu | Asp | Tyr | Ala | Lys | Glu | Gly |     |
|     |     | 225 |     |     |     | 230 |     |     |     |     | 235 |     |     |     |     |     |
| TTC | CGT | GCT | CCT | CTT | CAA | TCT | AAA | TTG | GAT | GCC | AAA | AAA | GCT | AAA | CTA | 888 |
| Phe | Arg | Ala | Pro | Leu | Gln | Ser | Lys | Leu | Asp | Ala | Lys | Lys | Ala | Lys | Leu |     |
|     | 240 |     |     |     | 245 |     |     |     |     | 250 |     |     |     |     |     |     |
| TCA | AAA | CTT | GAA | GAG | TTA | AGT | GAT | AAG | ATT | GAT | GAG | TTA | GAC | GCT | GAA | 936 |
| Ser | Lys | Leu | Glu | Glu | Leu | Ser | Asp | Lys | Ile | Asp | Glu | Leu | Asp | Ala | Glu |     |
| 255 |     |     |     | 260 |     |     |     |     | 265 |     |     |     |     | 270 |     |     |
| ATT | GCA | AAA | CTT | GAA | GAT | CAA | CTT | AAA | GCT | GCT | GAA | GAA | AAC | AAT | AAT | 984 |
| Ile | Ala | Lys | Leu | Glu | Asp | Gln | Leu | Lys | Ala | Ala | Glu | Glu | Asn | Asn | Asn |     |
|     |     |     |     | 275 |     |     |     |     | 280 |     |     |     |     | 285 |     |     |
| GTA | GAA | GAC | TAC | TTT | AAA | GAA | GGT | TTA | GAG | AAA | ACT | ATT | GCT | GCT | AAA | 1032 |
| Val | Glu | Asp | Tyr | Phe | Lys | Glu | Gly | Leu | Glu | Lys | Thr | Ile | Ala | Ala | Lys |     |
|     |     |     | 290 |     |     |     |     | 295 |     |     |     |     | 300 |     |     |     |
| AAA | GCT | GAA | TTA | GAA | AAA | ACT | GAA | GCT | GAC | CTT | AAG | AAA | GCA | GTT | AAT | 1080 |
| Lys | Ala | Glu | Leu | Glu | Lys | Thr | Glu | Ala | Asp | Leu | Lys | Lys | Ala | Val | Asn |     |
|     |     | 305 |     |     |     |     | 310 |     |     |     |     | 315 |     |     |     |     |
| GAG | CCA | GAA | AAA | CCA | GCT | CCA | GCT | CCA | GAA | ACT | CCA | GCC | CCA | GAA | GCA | 1128 |
| Glu | Pro | Glu | Lys | Pro | Ala | Pro | Ala | Pro | Glu | Thr | Pro | Ala | Pro | Glu | Ala |     |
|     | 320 |     |     |     | 325 |     |     |     |     | 330 |     |     |     |     |     |     |
| CCA | GCT | GAA | CAA | CCA | AAA | CCA | GCG | CCG | GCT | CCT | CAA | CCA | GCT | CCC | GCA | 1176 |
| Pro | Ala | Glu | Gln | Pro | Lys | Pro | Ala | Pro | Ala | Pro | Gln | Pro | Ala | Pro | Ala |     |
| 335 |     |     |     |     | 340 |     |     |     |     | 345 |     |     |     |     | 350 |     |
| CCA | AAA | CCA | GAG | AAG | CCA | GCT | GAA | CAA | CCA | AAA | CCA | GAA | AAA | ACA | GAT | 1224 |
| Pro | Lys | Pro | Glu | Lys | Pro | Ala | Glu | Gln | Pro | Lys | Pro | Glu | Lys | Thr | Asp |     |
|     |     |     |     | 355 |     |     |     |     | 360 |     |     |     |     | 365 |     |     |
| GAT | CAA | CAA | GCT | GAA | GAA | GAC | TAT | GCT | CGT | AGA | TCA | GAA | GAA | GAA | TAT | 1272 |
| Asp | Gln | Gln | Ala | Glu | Glu | Asp | Tyr | Ala | Arg | Arg | Ser | Glu | Glu | Glu | Tyr |     |
|     |     |     | 370 |     |     |     |     | 375 |     |     |     |     | 380 |     |     |     |
| AAT | CGC | TTG | ACT | CAA | CAG | CAA | CCG | CCA | AAA | GCT | GAA | AAA | CCA | GCT | CCT | 1320 |
| Asn | Arg | Leu | Thr | Gln | Gln | Gln | Pro | Pro | Lys | Ala | Glu | Lys | Pro | Ala | Pro |     |
|     |     | 385 |     |     |     |     | 390 |     |     |     |     | 395 |     |     |     |     |
| GCA | CCA | AAA | ACA | GGC | TGG | AAA | CAA | GAA | AAC | GGT | ATG | TGG | TAC | TTC | TAC | 1368 |
| Ala | Pro | Lys | Thr | Gly | Trp | Lys | Gln | Glu | Asn | Gly | Met | Trp | Tyr | Phe | Tyr |     |
|     | 400 |     |     |     |     | 405 |     |     |     |     | 410 |     |     |     |     |     |
| AAT | ACT | GAT | GGT | TCA | ATG | GCG | ACA | GGA | TGG | CTC | CAA | AAC | AAC | GGT | TCA | 1416 |
| Asn | Thr | Asp | Gly | Ser | Met | Ala | Thr | Gly | Trp | Leu | Gln | Asn | Asn | Gly | Ser |     |
| 415 |     |     |     |     | 420 |     |     |     |     | 425 |     |     |     |     | 430 |     |
| TGG | TAC | TAC | CTC | AAC | AGC | AAT | GGT | GCT | ATG | GCT | ACA | GGT | TGG | CTC | CAA | 1464 |
| Trp | Tyr | Tyr | Leu | Asn | Ser | Asn | Gly | Ala | Met | Ala | Thr | Gly | Trp | Leu | Gln |     |
|     |     |     |     | 435 |     |     |     |     | 440 |     |     |     |     | 445 |     |     |
| TAC | AAT | GGT | TCA | TGG | TAT | TAC | CTC | AAC | GCT | AAC | GGC | GCT | ATG | GCA | ACA | 1512 |
| Tyr | Asn | Gly | Ser | Trp | Tyr | Tyr | Leu | Asn | Ala | Asn | Gly | Ala | Met | Ala | Thr |     |
|     |     |     | 450 |     |     |     |     | 455 |     |     |     |     | 460 |     |     |     |
| GGT | TGG | GCT | AAA | GTC | AAC | GGT | TCA | TGG | TAC | TAC | CTC | AAC | GCT | AAT | GGT | 1560 |
| Gly | Trp | Ala | Lys | Val | Asn | Gly | Ser | Trp | Tyr | Tyr | Leu | Asn | Ala | Asn | Gly |     |
|     |     | 465 |     |     |     |     | 470 |     |     |     |     | 475 |     |     |     |     |
| GCT | ATG | GCT | ACA | GGT | TGG | CTC | CAA | TAC | AAC | GGT | TCA | TGG | TAT | TAC | CTC | 1608 |
| Ala | Met | Ala | Thr | Gly | Trp | Leu | Gln | Tyr | Asn | Gly | Ser | Trp | Tyr | Tyr | Leu |     |
|     | 480 |     |     |     |     | 485 |     |     |     |     | 490 |     |     |     |     |     |
| AAC | GCT | AAC | GGC | GCT | ATG | GCA | ACA | GGT | TGG | GCT | AAA | GTC | AAC | GGT | TCA | 1656 |
| Asn | Ala | Asn | Gly | Ala | Met | Ala | Thr | Gly | Trp | Ala | Lys | Val | Asn | Gly | Ser |     |
| 495 |     |     |     |     | 500 |     |     |     |     | 505 |     |     |     |     | 510 |     |
| TGG | TAC | TAC | CTC | AAC | GCT | AAT | GGT | GCT | ATG | GCT | ACA | GGT | TGG | CTC | CAA | 1704 |
| Trp | Tyr | Tyr | Leu | Asn | Ala | Asn | Gly | Ala | Met | Ala | Thr | Gly | Trp | Leu | Gln |     |
|     |     |     |     | 515 |     |     |     |     | 520 |     |     |     |     | 525 |     |     |

| | | | | | | | | | | | | | | | | |
|---|---|---|---|---|---|---|---|---|---|---|---|---|---|---|---|---|
| TAC | AAC | GGT | TCA | TGG | TAC | TAC | CTC | AAC | GCT | AAC | GGT | GCT | ATG | GCT | ACA | 1752 |
| Tyr | Asn | Gly | Ser | Trp | Tyr | Tyr | Leu | Asn | Ala | Asn | Gly | Ala | Met | Ala | Thr | |
| | | | 530 | | | | 535 | | | | | 540 | | | | |
| GGT | TGG | GCT | AAA | GTC | AAC | GGT | TCA | TGG | TAC | TAC | CTC | AAC | GCT | AAT | GGT | 1800 |
| Gly | Trp | Ala | Lys | Val | Asn | Gly | Ser | Trp | Tyr | Tyr | Leu | Asn | Ala | Asn | Gly | |
| | | 545 | | | | | 550 | | | | | | 555 | | | |
| GCT | ATG | GCA | ACA | GGT | TGG | GTG | AAA | GAT | GGA | GAT | ACC | TGG | TAC | TAT | CTT | 1848 |
| Ala | Met | Ala | Thr | Gly | Trp | Val | Lys | Asp | Gly | Asp | Thr | Trp | Tyr | Tyr | Leu | |
| | 560 | | | | | 565 | | | | | 570 | | | | | |
| GAA | GCA | TCA | GGT | GCT | ATG | AAA | GCA | AGC | CAA | TGG | TTC | AAA | GTA | TCA | GAT | 1896 |
| Glu | Ala | Ser | Gly | Ala | Met | Lys | Ala | Ser | Gln | Trp | Phe | Lys | Val | Ser | Asp | |
| 575 | | | | | 580 | | | | | 585 | | | | | 590 | |
| AAA | TGG | TAC | TAT | GTC | AAT | GGT | TTA | GGT | GCC | CTT | GCA | GTC | AAC | ACA | ACT | 1944 |
| Lys | Trp | Tyr | Tyr | Val | Asn | Gly | Leu | Gly | Ala | Leu | Ala | Val | Asn | Thr | Thr | |
| | | | | 595 | | | | 600 | | | | | | 605 | | |
| GTA | GAT | GGC | TAT | AAA | GTC | AAT | GCC | AAT | GGT | GAA | TGG | GTT | TAA | GCC | GAT | 1992 |
| Val | Asp | Gly | Tyr | Lys | Val | Asn | Ala | Asn | Gly | Glu | Trp | Val | | Ala | Asp | |
| | | | 610 | | | | | 615 | | | | | | 620 | | |
| TAA | ATT | AAA | GCA | TGT | TAA | GAA | CAT | TTG | ACA | TTT | TAA | TTT | TGA | AAC | AAA | 2040 |
| | Ile | Lys | Ala | Cys | | Glu | His | Leu | Thr | Phe | | Phe | | Asn | Lys | |
| | | | | 625 | | | | | | 630 | | | | | | |
| GAT | AAG | GTT | CGA | TTG | AAT | AGA | TTT | ATG | TTC | GTA | TTC | TTT | AGG | TAC | | 2085 |
| Asp | Lys | Val | Arg | Leu | Asn | Arg | Phe | Met | Phe | Val | Phe | Phe | Arg | Tyr | | |
| | 635 | | | | | 640 | | | | | 645 | | | | | |

( 2 ) INFORMATION FOR SEQ ID NO:2:

( i ) SEQUENCE CHARACTERISTICS:
( A ) LENGTH: 648 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asn | Lys | Lys | Lys | Met | Ile | Leu | Thr | Ser | Leu | Ala | Ser | Val | Ala | Ile |
| 1 | | | | 5 | | | | | 10 | | | | | 15 | |
| Leu | Gly | Ala | Gly | Phe | Val | Ala | Ser | Gln | Pro | Thr | Val | Val | Arg | Ala | Glu |
| | | | 20 | | | | | 25 | | | | | 30 | | |
| Glu | Ser | Pro | Val | Ala | Ser | Gln | Ser | Lys | Ala | Glu | Lys | Asp | Tyr | Asp | Ala |
| | | 35 | | | | | 40 | | | | | 45 | | | |
| Ala | Lys | Lys | Asp | Ala | Lys | Asn | Ala | Lys | Lys | Ala | Val | Glu | Asp | Ala | Gln |
| | 50 | | | | | 55 | | | | | 60 | | | | |
| Lys | Ala | Leu | Asp | Asp | Ala | Lys | Ala | Ala | Gln | Lys | Lys | Tyr | Asp | Glu | Asp |
| 65 | | | | | 70 | | | | | 75 | | | | | 80 |
| Gln | Lys | Lys | Thr | Glu | Glu | Lys | Ala | Ala | Leu | Glu | Lys | Ala | Ala | Ser | Glu |
| | | | | 85 | | | | | 90 | | | | | 95 | |
| Glu | Met | Asp | Lys | Ala | Val | Ala | Ala | Val | Gln | Gln | Ala | Tyr | Leu | Ala | Tyr |
| | | | 100 | | | | | 105 | | | | | 110 | | |
| Gln | Gln | Ala | Thr | Asp | Lys | Ala | Ala | Lys | Asp | Ala | Ala | Asp | Lys | Met | Ile |
| | | 115 | | | | | 120 | | | | | 125 | | | |
| Asp | Glu | Ala | Lys | Lys | Arg | Glu | Glu | Ala | Lys | Thr | Lys | Phe | Asn | Thr | |
| | 130 | | | | | 135 | | | | | 140 | | | | |
| Val | Arg | Ala | Met | Val | Val | Pro | Glu | Pro | Glu | Gln | Leu | Ala | Glu | Thr | Lys |
| 145 | | | | | 150 | | | | | 155 | | | | | 160 |
| Lys | Lys | Ser | Glu | Glu | Ala | Lys | Gln | Lys | Ala | Pro | Glu | Leu | Thr | Lys | Lys |
| | | | | 165 | | | | | 170 | | | | | 175 | |
| Leu | Glu | Glu | Ala | Lys | Ala | Lys | Leu | Glu | Glu | Ala | Glu | Lys | Lys | Ala | Thr |
| | | | 180 | | | | | 185 | | | | | 190 | | |

-continued

| | | | | | | | | | | | | | |
|---|---|---|---|---|---|---|---|---|---|---|---|---|---|
| Glu | Ala | Lys | Gln | Lys | Val | Asp | Ala | Glu | Glu | Val | Ala | Pro | Gln | Ala | Lys |
| | | 195 | | | | | 200 | | | | | 205 | | | |
| Ile | Ala | Glu | Leu | Glu | Asn | Gln | Val | His | Arg | Leu | Glu | Gln | Glu | Leu | Lys |
| | 210 | | | | | 215 | | | | | 220 | | | | |
| Glu | Ile | Asp | Glu | Ser | Glu | Ser | Glu | Asp | Tyr | Ala | Lys | Glu | Gly | Phe | Arg |
| 225 | | | | | 230 | | | | | 235 | | | | | 240 |
| Ala | Pro | Leu | Gln | Ser | Lys | Leu | Asp | Ala | Lys | Lys | Ala | Lys | Leu | Ser | Lys |
| | | | | 245 | | | | | 250 | | | | | 255 | |
| Leu | Glu | Glu | Leu | Ser | Asp | Lys | Ile | Asp | Glu | Leu | Asp | Ala | Glu | Ile | Ala |
| | | | 260 | | | | | 265 | | | | | 270 | | |
| Lys | Leu | Glu | Asp | Gln | Leu | Lys | Ala | Ala | Glu | Glu | Asn | Asn | Asn | Val | Glu |
| | | 275 | | | | | 280 | | | | | 285 | | | |
| Asp | Tyr | Phe | Lys | Glu | Gly | Leu | Glu | Lys | Thr | Ile | Ala | Ala | Lys | Lys | Ala |
| | 290 | | | | | 295 | | | | | 300 | | | | |
| Glu | Leu | Glu | Lys | Thr | Glu | Ala | Asp | Leu | Lys | Lys | Ala | Val | Asn | Glu | Pro |
| 305 | | | | | 310 | | | | | 315 | | | | | 320 |
| Glu | Lys | Pro | Ala | Pro | Ala | Pro | Glu | Thr | Pro | Ala | Pro | Glu | Ala | Pro | Ala |
| | | | | 325 | | | | | 330 | | | | | 335 | |
| Glu | Gln | Pro | Lys | Pro | Ala | Pro | Ala | Pro | Gln | Pro | Ala | Pro | Ala | Pro | Lys |
| | | | 340 | | | | | 345 | | | | | 350 | | |
| Pro | Glu | Lys | Pro | Ala | Glu | Gln | Pro | Lys | Pro | Glu | Lys | Thr | Asp | Asp | Gln |
| | | 355 | | | | | 360 | | | | | 365 | | | |
| Gln | Ala | Glu | Glu | Asp | Tyr | Ala | Arg | Arg | Ser | Glu | Glu | Tyr | Asn | Arg |
| | 370 | | | | | 375 | | | | | 380 | | | | |
| Leu | Thr | Gln | Gln | Gln | Pro | Pro | Lys | Ala | Glu | Lys | Pro | Ala | Pro | Ala | Pro |
| 385 | | | | | 390 | | | | | 395 | | | | | 400 |
| Lys | Thr | Gly | Trp | Lys | Gln | Glu | Asn | Gly | Met | Trp | Tyr | Phe | Tyr | Asn | Thr |
| | | | | 405 | | | | | 410 | | | | | 415 | |
| Asp | Gly | Ser | Met | Ala | Thr | Gly | Trp | Leu | Gln | Asn | Asn | Gly | Ser | Trp | Tyr |
| | | | 420 | | | | | 425 | | | | | 430 | | |
| Tyr | Leu | Asn | Ser | Asn | Gly | Ala | Met | Ala | Thr | Gly | Trp | Leu | Gln | Tyr | Asn |
| | | 435 | | | | | 440 | | | | | 445 | | | |
| Gly | Ser | Trp | Tyr | Tyr | Leu | Asn | Ala | Asn | Gly | Ala | Met | Ala | Thr | Gly | Trp |
| | 450 | | | | | 455 | | | | | 460 | | | | |
| Ala | Lys | Val | Asn | Gly | Ser | Trp | Tyr | Tyr | Leu | Asn | Ala | Asn | Gly | Ala | Met |
| 465 | | | | | 470 | | | | | 475 | | | | | 480 |
| Ala | Thr | Gly | Trp | Leu | Gln | Tyr | Asn | Gly | Ser | Trp | Tyr | Tyr | Leu | Asn | Ala |
| | | | | 485 | | | | | 490 | | | | | 495 | |
| Asn | Gly | Ala | Met | Ala | Thr | Gly | Trp | Ala | Lys | Val | Asn | Gly | Ser | Trp | Tyr |
| | | | 500 | | | | | 505 | | | | | 510 | | |
| Tyr | Leu | Asn | Ala | Asn | Gly | Ala | Met | Ala | Thr | Gly | Trp | Leu | Gln | Tyr | Asn |
| | | 515 | | | | | 520 | | | | | 525 | | | |
| Gly | Ser | Trp | Tyr | Tyr | Leu | Asn | Ala | Asn | Gly | Ala | Met | Ala | Thr | Gly | Trp |
| | 530 | | | | | 535 | | | | | 540 | | | | |
| Ala | Lys | Val | Asn | Gly | Ser | Trp | Tyr | Tyr | Leu | Asn | Ala | Asn | Gly | Ala | Met |
| 545 | | | | | 550 | | | | | 555 | | | | | 560 |
| Ala | Thr | Gly | Trp | Val | Lys | Asp | Gly | Asp | Thr | Trp | Tyr | Tyr | Leu | Glu | Ala |
| | | | | 565 | | | | | 570 | | | | | 575 | |
| Ser | Gly | Ala | Met | Lys | Ala | Ser | Gln | Trp | Phe | Lys | Val | Ser | Asp | Lys | Trp |
| | | | 580 | | | | | 585 | | | | | 590 | | |
| Tyr | Tyr | Val | Asn | Gly | Leu | Gly | Ala | Leu | Ala | Val | Asn | Thr | Thr | Val | Asp |
| | | 595 | | | | | 600 | | | | | 605 | | | |
| Gly | Tyr | Lys | Val | Asn | Ala | Asn | Gly | Glu | Trp | Val | Ala | Asp | Ile | Lys | Ala |
| | 610 | | | | | 615 | | | | | 620 | | | | |

```
Cys Glu His Leu Thr Phe Phe Asn Lys Asp Lys Val Arg Leu Asn Arg
625                 630                 635                 640

Phe Met Phe Val Phe Phe Arg Tyr
                645
```

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:3:

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys
            35                  40                  45
```

( 2 ) INFORMATION FOR SEQ ID NO:4:

( i ) SEQUENCE CHARACTERISTICS:
        ( A ) LENGTH: 289 amino acids
        ( B ) TYPE: amino acid
        ( C ) STRANDEDNESS: single
        ( D ) TOPOLOGY: linear ( v ) FRAGMENT TYPE: N-terminal ( x i ) SEQUENCE DESCRIPTION: SEQ ID NO:4:

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
            35                  40                  45

Asp Gln Lys Lys Thr Glu Glu Lys Ala Ala Leu Glu Lys Ala Ala Ser
    50              55                  60

Glu Glu Met Asp Lys Ala Val Ala Ala Val Gln Gln Ala Tyr Leu Ala
65              70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Ala Lys Thr Lys Phe Asn
                100             105                 110

Thr Val Arg Ala Met Val Val Pro Glu Pro Glu Gln Leu Ala Glu Thr
            115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Glu Asp Tyr Ala Lys Glu Gly
            195                 200                 205

Phe Arg Ala Pro Leu Gln Ser Lys Leu Asp Ala Lys Lys Ala Lys Leu
    210                 215                 220
```

| Ser | Lys | Leu | Glu | Glu | Leu | Ser | Asp | Lys | Ile | Asp | Glu | Leu | Asp | Ala | Glu |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ile | Ala | Lys | Leu | Glu | Asp | Gln | Leu | Lys | Ala | Ala | Glu | Glu | Asn | Asn | Asn |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Val | Glu | Asp | Tyr | Phe | Lys | Glu | Gly | Leu | Glu | Lys | Thr | Ile | Ala | Ala | Lys |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Lys | Ala | Glu | Leu | Glu | Lys | Thr | Glu | Ala | Asp | Leu | Lys | Lys | Ala | Val | Asn |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

Glu ( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CCGGATCCAG CTCCTGCACC AAAAAC    26

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCGCTGCGAC GGCTTAAACC CATTCACCAT TGG    33

STRUCTURAL GENE OF PNEUMOCOCCAL PROTEIN

REFERENCE TO RELATED APPLICATION

This application is a continuation of application Ser. No. 08/072,065, filed Jun. 3, 1993 (now abandoned) which is a divisional of application on Ser. No. 07/835,698 filed Feb. 12, 1992 (now abandoned), which is a continuation-in-part application Ser. No. 07/656,773 filed on Feb. 15, 1991 (now abandoned).

FIELD OF INVENTION

The present invention is concerned with the development of an improved vaccine against pneumococcal infections.

BACKGROUND TO THE INVENTION

*Streptococcus pneumoniae* is an important cause of otitis media, meningitis, bacteremia and pneumonia. Despite the use of antibiotics and vaccines, the prevalence of pneumococcal infections has declined little over the last twenty-five years.

It is generally accepted that immunity to *Streptococcus pneumoniae* can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to protein to make them immunogenic. This approach has been successful, for example, with *Haemophilus influenzae b* (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J.Exp.Med. 160:386–397, 1984, there is described the production of hybridoma antibodies that recognize cell surface polypeptide(s) on *S. pneumoniae* and protection of mice from infection with certain strains of encapsulated pneumococci by such antibodies. This surface protein antigen has been termed "pneumococcal surface protein A" or PspA for short.

In McDaniel et al (II), Microbial Pathogenesis 1:519–531, 1986, there are described studies on the characterization of the PspA. Considerable diversity in the PspA molecule in different strains was found, as were differences in the epitopes recognized by different antibodies.

In McDaniel et al (III), J.Exp.Med. 165:381–394, 1987, there is disclosed that immunization of X-linked immunodeficient (XID) mice with non-encapsulated pneumococci expressing PspA, but not isogenic pneumococci lacking PspA, protects mice from subsequent fatal infection with pneumococci.

In McDaniel et al (IV), Infect. Immun., 59:222–228, 1991, there is described immunization of mice with a recombinant full length fragment of PspA that is able to elicit protection against pneumococcal strains of capsular types 6A and 3.

In Crain et al, Infect.Immun., 56:3293–3299, 1990, there is described a rabbit antiserum that detects PspA in 100% (n=95) of clinical and laboratory isolates of strains of *S. pneumoniae*. When reacted with seven monoclonal antibodies to PspA, fifty-seven *S. pneumoniae* isolates exhibited thirty-one different patterns of reactivity.

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant 1 gt11 clone, elicited protection against challenge with several *S. pneumoniae* strains representing different capsular and PspA types, as described in McDaniel et al (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of *S. pneumoniae* strains.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 1989;

2. Abstracts of 90th Annual Meeting of the American Society for Microbiology, p. 98, item D-106, May 1990;

3. Abstracts of 3rd International ASM Conference on Streptococcal Genetics, p. 11, item 12, June 1990;

4. Talkington et al, Infect. Immun. 59:1285–1289, 1991;

5. Yother et al, J. Bacteriol. 174:601–609, 1992; and

6. Yother et al, J. Bacteriol. 174:610–618, 1992.

The latter three publications occurred after the filing of the aforesaid U.S. Ser. No. 656,773.

In the specification which follows and the drawings accompanying the same, there are utilized certain accepted abbreviations with respect to the amino acids represented thereby. The following Table I identifies those abbreviations:

TABLE I

| AMINO ACID ABBREVIATIONS | |
|---|---|
| A = Ala = Alanine | M = Met = Methionine |
| C = Cys = Cysteine | N = Asn = Asparagine |
| D = Asp = Aspartic Acid | P = Pro = Proline |
| E = Glu = Glutamic Acid | Q = Gln = Glutamine |
| F = Phe = Phenylalanine | R = Arg = Arginine |

TABLE I-continued

AMINO ACID ABBREVIATIONS

| | |
|---|---|
| G = Gly = Glycine | S = Ser = Serine |
| H = His = Histidine | T = Thr = Threonine |
| I = Ile = Isoleucine | V = Val = Valine |
| K = Lys = Lysine | W = Try = Tryptophan |
| L = Leu = Leucine | Y = Tyr = Tyrosine |

SUMMARY OF INVENTION

The present invention relates to the preparation of mutants of S. pneumoniae that secrete an immunogenic truncated form of the PspA protein, and isolation and purification of the secreted protein. The truncated form of the PspA protein is immunoprotective and contains the protective epitopes of PspA. The PspA protein is soluble in physiologic solution and lacking at least the functional cell membrane anchor region.

BRIEF DESCRIPTION OF DRAWINGS

FIGS. 3A–C is the DNA sequence of the pspA gene (SEQ ID NO. 1) with deduced amino acid sequence for the PspA protein (see SEQ ID NO. 2);

FIGS. 4A–B depicts the restriction map of pspA (FIG. 4A) and the use of insertion-duplication mutagenesis to construct mutations in the pspA gene (FIG. 4B).

FIG. 5 shows the deduced amino acid sequence for the N-terminal region of PspA (SEQ ID No. 4) and the general location of epitopes recognized by monoclonal antibodies;

FIG. 6 shows antibody reactivity with PspA fragments produced by various pspA gene segments.

GENERAL DESCRIPTION OF INVENTION

According to one aspect of the present invention, there is provided a purified immunoprotective pneumococcal surface protein, comprising a truncated form of PspA which contains the immunoprotective epitopes of the protein and up to about 90% of the whole PspA protein and from which the functional cell membrane anchor region is absent.

Through the technique of insertion-duplication mutagenesis of the pspA gene of the strain Rx1 of Streptococcus pneumoniae with plasmids containing cloned fragments of the pspA structural gene, it has been possible to produce soluble fragments of PspA that are secreted by pneumococci.

In another aspect of the present invention, therefore, there is provided a method of forming an immunoprotective truncated PspA protein, which comprises effecting insertion-duplication mutagenesis of a bacterium with a pspA gene resulting in the coding of a truncated expressible PspA protein, growing the mutated bacterium to effect expression of a truncated PspA protein, and isolating the protein.

The molecular size of the purified truncated PspA protein obtained may be varied by directing the point of insertion, which determines the termination of gene expression, to different points in the pspA gene. For example, an N-terminal fragment of apparent molecular weight of 43 kD, constituting approximately one-half of the native protein, has been found useful.

The truncated segment which is produced by this procedure is capable of eliciting protection in mice from fatal challenge with type 3 S. pneumoniae, demonstrating for the first time that a purified PspA can elicit protection and that this truncated segment of the protein contains protective epitopes of PspA.

Figures 1, 2:
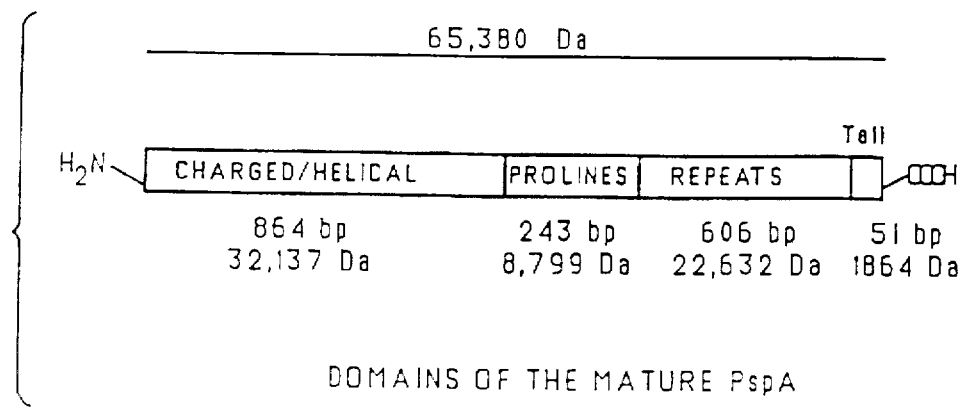
FIG. 1 is a schematic representation of the domains of the mature PspA.
FIG. 2 is the N-terminal amino acid sequence of PspA (SEQ ID NO: 3), wherein upper case letters denote charged hydrophilic amino acids, lower-case letters designate apolar, hydrophobic residues, and underlined bold lower case letters denote uncharged, polar, hydrophilic residues.

Amino acid sequence information was obtained on the N-terminal 45 amino acids of the truncated segment of PspA. This sequence is shown in FIG. 2 (SEQ ID NO: 3). Predictive secondary structural analysis shows that this sequence has a very strong alpha-helical formation, with no non-helical inserts. About 51% of the segment is composed only of two amino acids, namely lysine, a charged amino acid, and alanine, a non-polar amino acid.

Analysis of this 45-amino acid sequence also reveals that it contains a seven-residue periodicity (see FIG. 2). In PspA, the periodicity begins with residue 8 and extends throughout the entire sequence, for nearly eleven turns of the helix. Positions "a" and "d" are occupied by apolar amino acids and position "b", "c" and "f" generally contain hydrophilic amino acids. Position "f" is predominantly occupied by lysine. Having regard to these observations, this region of PspA is very likely in an alpha-helical coiled-coil configuration. The deduced amino acid sequence for the whole of the α-helical coiled-coil region is shown in FIG. 5 (SEQ ID NO: 1).

Figure 3B:
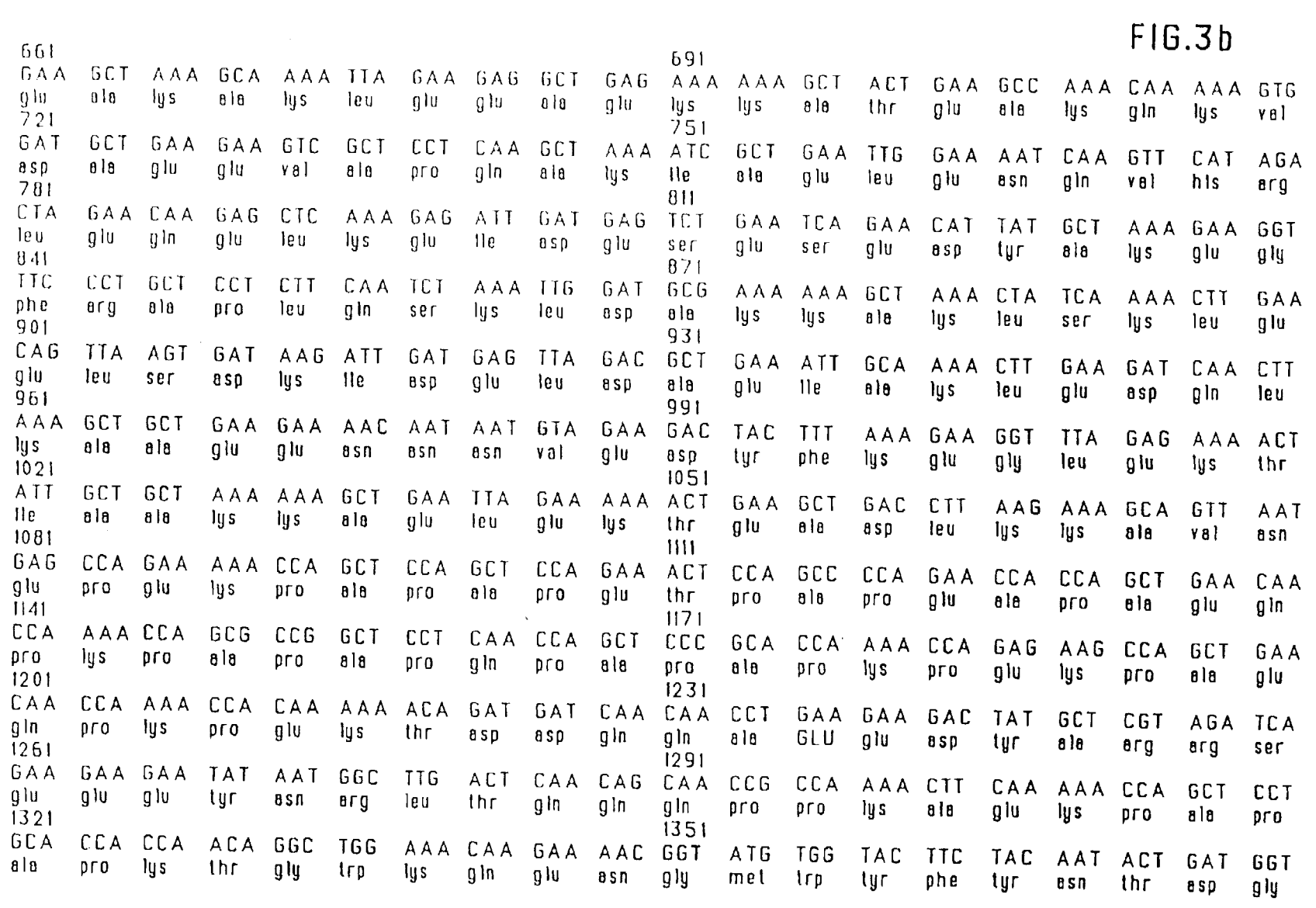

We also have cloned and sequenced the entire coding region of pspA (see FIG. 3 (SEQ ID NO: 1)). The deduced amino acid sequence for the PspA protein reveals three distinct regions of the PspA molecule, shown schematically in FIG. 1. Accordingly, a further aspect of the present invention, there is provided a biologically-pure recombinant DNA molecule coding for the PspA protein or portions thereof and having a coding sequence included within set forth in FIGS. 3A–C (SEQ ID NO: 1) or having substantial homology thereto.

The DNA sequence of the pspA gene is contained on a HindIII-KpnI fragment that is 2086 base pairs in length. The pspA gene itself represents approximately 1985 base pairs of this fragment, and comprises an initial region containing transcription and translational signals with translation starting at the ATG/met (nucleotide position 127), followed by a leader sequence extending from the ATG/met (nucleotide position 127) to GCA/ala (nucleotide position 217). Mature Pspa starts with the glu amino acid at nucleotide position 220 and ends at the translational stop TAA/OCH at nucleotide position 1984. This translational stop codon is followed by transcription termination signals.

The amino terminal of the protein sequence, predicted from the DNA sequence of FIG. 3 (SEQ ID NO: 2), contains a 31 amino acid leader sequence and a 45 amino acid sequence identical to the 45 amino acid sequence of the N-terminal of PspA (FIG. 2 (SEQ ID NO: 3)). The amino end of the predicted protein sequence is highly charged and α-helical in nature. This region has homology with tropomyosin at the amino acid level (approximately 22% identity and 50% similarity). This homology is due largely to a repeating seven residue periodicity where the first and fourth amino acids are hydrophobic, the intervening amino acids are helix-promoting and the seventh amino acid is charged. This pattern is consistent with that of an α-helical coiled-coil molecule and indicates that the α-helical coil extends through the N-terminal half of the molecule. The amino acid sequence of the whole of the α-helical coil region is shown in FIG. 5 (SEQ ID NO: 4).

Following the charged helical region is a proline-rich region in which 23 of 81 amino acids are prolines. Immediately carboxy to the proline-rich region is the first of ten highly homologous twenty amino acid repeats. The only significantly hydrophobic region in the sequenced portion of the molecule begins at the last repeat. This potential membrane-spanning region contains several charged amino acids preceding the translational stop codon.

The insertionally-inactivated mutants of *S. pneumoniae* lacking the C-terminal anchor regions are capable of growth in chemically-defined medium and secrete the N-terminal portion of the PspA protein into the medium. The N-terminal region of PspA is highly soluble in the culture medium and is much easier to isolate than the entire molecule. Soluble truncated molecules have been produced using insertional duplicational mutagenesis directed by the cloned PspA DNA fragments shown in FIGS. 4A–B. Expression of the same truncated construct (with the pneumococcal promoter) in *E. coli* results in the same PspA fragment being secreted into the periplasm of *E. coli*. PspA is readily released from the periplasm by hypotonic lysis.

Truncated PspA is isolated from culture medium of mutant pneumococci in any convenient manner, such as by tangential flow filtration. Ion-exchange chromatography then is performed on an anionic resin to purify the protein. In this procedure, the solution containing PspA is dialyzed to pH6 in 0.02M salt solution and passed over the resin. The PspA is eluted from the resin with a gradient of 0.08 to 2.0M ionic strength and is collected in the fraction between 0.34 and 0.87M ionic strength, depending on the nature of the column used.

The PspA may be further purified by sodium dodecyl sulfate polyacrylamide gel (SDS-PAGE) electrophoresis. The PspA-containing portion of the gel is identified by staining of the gel and PspA is electroeluted from this portion.

The electrophoresis purification is convenient when only small quantities of PspA are being handled. As an alternative, more suited to large-scale production; the protein may be purified by size chromatography in a pH7 phosphate buffer.

Since it is possible to obtain expression of the truncated form of PspA into the culture medium, as opposed to it being trapped within the cell wall and making purification much more complicated, it is possible to isolate other proteins that have been cloned into the truncated pspA gene by making fusion proteins between PspA and other proteins. Such a technique may be employed to enhance the immunogenicity or preserve the immunogenic structural conformation or presentation of the gene product, to permit the fusion protein to be used in immunization, which may be systemic and/or mucosal, against disease.

One example of such a fusion protein is a fusion of the soluble N-terminal region of PspA and the B-subunit of cholera toxin. Fusion proteins also may be formed by chemical attachment of the truncated PspA protein to other proteins.

Another aspect of the present invention, therefore, provides a method for the production of cloned proteins, which comprises fusing a pspA gene coding for a truncated form of PspA protein with the gene coding for another protein to form a fusion protein clone, transforming *S. pneumoniae*, *E. coli* or other bacteria with the fusion protein clone, growing the transformed bacterium to effect expression of a fusion protein comprising truncated PspA and the other protein into the culture medium, and isolating the fusion protein.

By using this technique, there can be produced cloned proteins in gram positive bacteria, such as pneumococci, for example, *S. pneumoniae*, and mycobacteria, for example, Bacille Calmette-Guerin (BCG). This approach overcomes the problems inherent in the production of proteins in gram negative bacteria, such as *E. coli*, usually used for cloning, in particular the need to purify the recombinant proteins from endotoxin and the toxicity of many gram positive DNA sequences in gram negative organisms.

For the expression of a fusion protein comprising the soluble N-terminal region of PspA and the B-subunit of cholera toxin (CTB), a gene fusion of a pspA gene coding for a truncated form of PspA protein with a ctxB gene coding for the B-subunit of cholera toxin is effected. Following expression of the fusion protein, the PspA and CTB may be cleaved one from another by dilute acid at an asparagine-proline sequence, known to be labile to dilute acid, engineered at the fusion site of the two proteins.

CTB is known to be highly specific for monosinloganglioside ($G_{M1}$). Accordingly, the fusion PspA-CTB protein may be isolated from the culture medium by adsorption to a $G_{M1}$ affinity column, from which the fusion protein subsequently may be eluted at low pH.

The PspA-CTB fusion protein finds considerable utility in solid phase immunoadsorbant assays. By using the fusion protein, it is possible to coat solid supports, such as microtitration plates, with PspA fragments without having first to isolate the PspA fragments. This may be done by adding bacterial extract containing the fusion protein to plates coated with $G_{M1}$. The PspA-CTB fusion protein then binds to $G_{M1}$ through the CTB moiety, thereby coating the solid support with PspA. The resulting coated product then may be used in a solid phase immunoadsorbant assay for the detection of PspA antibody and/or antigen in test samples. Such immunoadsorbant assays constitute an additional aspect of this invention.

The PspA attachment/anchor region, containing the proline-rich region, the repeat region and/or the C-terminus of PspA, also may be employed to effect expression of heterologous proteins in pneumococci, or other gram positive or gram negative bacteria in the which the attachment/ anchor region is functional. Generally, expression is effected on bacterial membrane, cell walls or cell surfaces in gram positive bacteria and in the periplasm of gram negative bacteria. An example of such heterologous protein is the B-subunit of cholera toxin.

As mentioned above, the truncated form of PspA provided herein contains the immunoprotective epitopes of the protein and hence is useful in a vaccine against pneumococcal infection. Accordingly, a yet further aspect of the present invention provides a vaccine against pneumococcal infection comprising, as an immunogenically-active component, the purified immunoprotective pneumococcal surface protein provided herein. The PspA protein may be employed as one component of a multicomponent vaccine which is effective in providing protection from a variety of infections.

In addition, gram positive bacteria which have been transformed to express the pspA gene coding for the truncated soluble PspA protein may be employed, in a live-attenuated or killed form, as an immunologically-active component of a vaccine against pneumococcal infection. In the transformed bacterium, such pspA gene may be fused to a gene coding for another protein. Accordingly, an additional aspect of this invention provides a vaccine against pneumococcal infection comprising, as an immunologically-active component, a live-attenuated or killed bacteria containing a gene coding for the truncated form of PspA.

The truncated form of PspA also may be employed in conjugates with normally weakly-immunogenic or non-immunogenic protection-eliciting molecules, such as various polysaccharides, to achieve immunogenic potentiation thereof. An additional aspect of the invention, therefore, provides a vaccine comprising, as an immunogenically-active component, a conjugate of the purified immunoprotective pneumococcal surface protein provided herein and a normally weakly-immunogenic or non-immunogenic protection-eliciting molecule.

Conserved sequences of pspA, particularly those in the proline-rich and/or repeat regions of the gene, may be employed as probes to detect the presence of pneumococci of various strains, through detection of pneumococcal DNA, in tissues, body fluids and/or secretions. Similarly, portions of the pspA gene may be used in diagnostic kits for the detection of pneumococcal infections.

In addition, primers made based on conserved sequences of pspA, particularly those in the proline-rich and/or repeat regions, may be used to assay for the presence of pneumococci in tissues, body fluids and/or secretions, through amplification of pneumococcal DNA. In this regard, a single primer pair derived from the nucleotide sequence of the pspA gene of *S. pneumoniae* may be employed in an assay using the polymerase chain reaction (PCR) for the specific detection of *Streptococcus pneumoniae*.

Specific amplification has been achieved of a 678 base pair DNA fragment from *S. pneumoniae* strain Rx1. After 30 cycles of amplification, the amplimer was detectable by agarose gel electrophoresis. The fragment was successfully amplified in all 32 strains of *S. pneumoniae* tested. PCR DNA amplification was able to detect less than an estimated 20 ficograms total genomic pneumococcal DNA.

Primers LSM1 (SEQ ID NO: 5) and LSM2, (SEQ ID NO: 6) having the nucleotide sequences:

LSM1 5'-CCGGATCCAGCTCCTGCACCAAAAC-3'

LSM2 5'-GCGCTGCGACGGCTTAAACCCATTCA-CCATTGG-3' amplified the 678 base pair product from pspA from nucleotides 1312 to 1990 of the Rx1 pspA sequence (FIGS. 3A–C; see SEQ ID NO: 1).

The PCR analysis using the primers described herein is performed in accordance with conventional PCR techniques, such as are described in the literature, for example, as described in Arnhem et al at C&EN Special Report, 36, Oct. 1, 1990. For detection purposes, the primer may be labelled or labelled nucleotide triphosphates may be included in the PCR reaction to label the PCR amplification product.

The PCR primers may be prepared by well-known methods, for example, by oligonucleotide synthesis or by fragmentation of a larger nucleotide sequence using suitable restriction enzymes.

The ability to use a single primer capable of detecting a large number of *S. pneumoniae* strains enables a universal PCR detection kit to be provided which is able to diagnose pneumococcal infection in mammals, including humans, independent of the strain which has caused the disease.

STRAINS, PLASMIDS AND PROBES

In the Examples which follow as well as in the accompanying drawings, reference is made to certain plasmids and bacterial strains transformed by such plasmids as well as vector DNA segments, some of which have been deposited with ATCC and all of which are fully described herein. The following Table II provides a summary of such materials.

TABLE II

Figure 7:
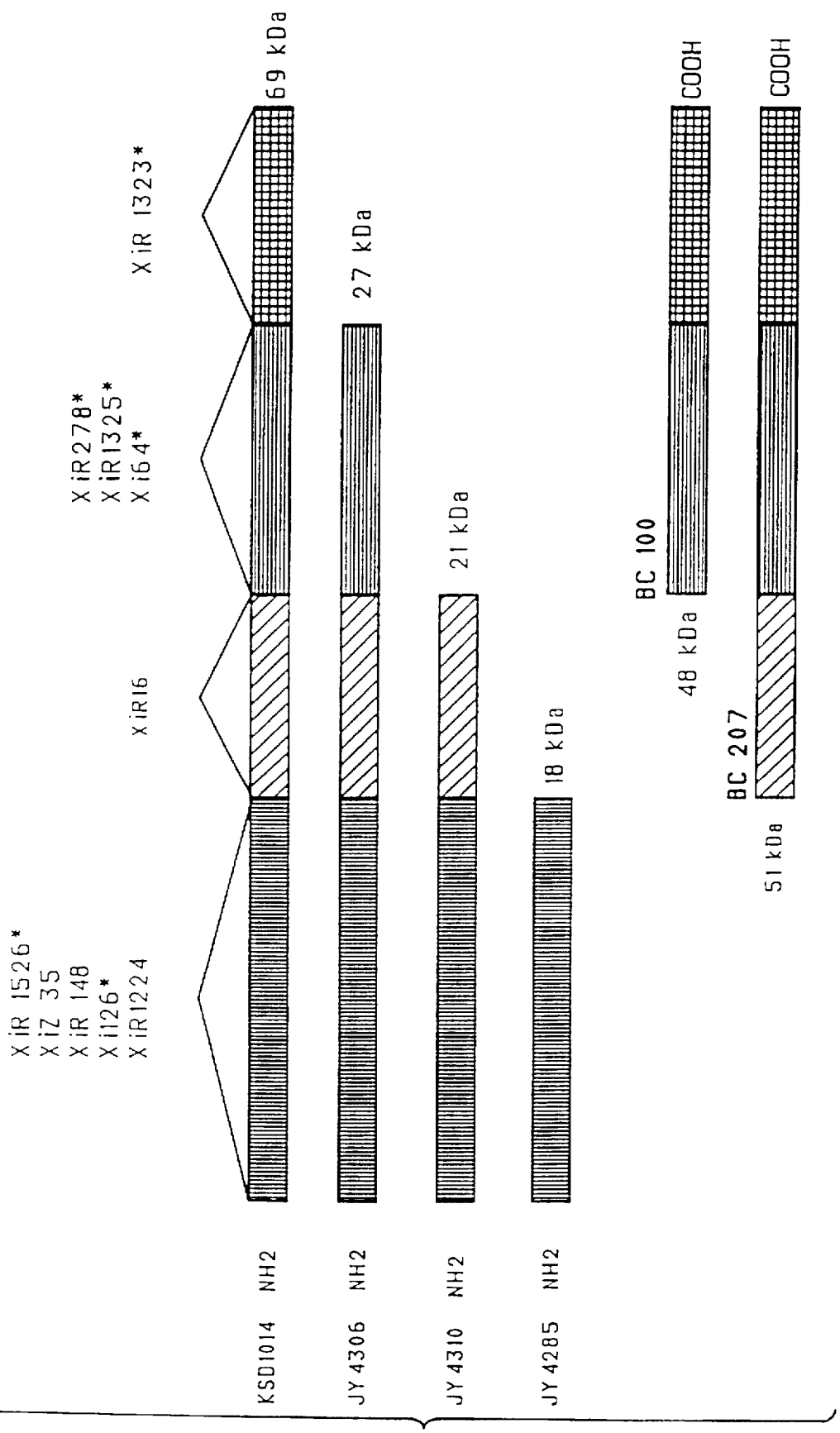
FIG. 7 shows the mapped location of epitopes in the PspA fragments produced by the different pspA gene segments.

| Identification | Type | Description | Deposit | Location |
| --- | --- | --- | --- | --- |
| JY4313 | *E. coli* strain | PspA DNA | ATCC 68529 | Example 1 |
| JY2008 | *S. pneumomiae* strain | PspA fragment 43 kDa | ATCC 55143 | Example 1 |
| JY4306 | *E. coli* strain | PspA fragment 43 kDa | ATCC 68522 | Example 3 |
| JY4310 | | PspA fragment 21 kDa | None | FIG. 7 |
| JY4285 | | PspA fragment 18 kDa | None | FIG. 7 |
| pJY4163 | Plasmid | Expression plasmid used for expression of PspA —CTB fusion protein (29 kDa) | None | Example 6 |
| JY4323 | DNA probe | HindIII-KpaI segment | None | Example 9 |
| JY4306 | DNA probe | HindIII-Dra-I segment | None | Example 9 |
| JY4262 | DNA probe | BclI-Bst-NI segment | None | Example 9 |

EXAMPLES

Example 1

This Example illustrates the preparation and growth of novel strains of *S. pneumoniae*.

The *S. pneumoniae* strain Rx1, which is a non-encapsulated derivative of capsular type 2 strain D39 (National Collection of Type Cultures, 61 Colindale Avenue London, WW95HT.UK NCTC #7466), was subjected to insertional inactivation (as described in McDaniel et al (III) 1987, Crain et al 1990, Talkington et al 1991, with 10 different cloned fragments of PspA (see FIG. 4). These fragments have all been obtained from restriction digests of cloned PspA DNA on a plasmid in *E. coli* strain JY4313 (deposited with the American Type Culture Collection 12301 Parklawn Drive, Rockville, Md. 20852 on Jan. 31, 1991 under ATCC accession number 68529). This insertional duplication mutagenesis (see FIG. 4) results in the termination of gene expression near the 3' end of the cloned fragment.

One of the resultant strains, JY2008 (deposited with the American Type Culture Collection on Jan. 24, 1991 under accession number 55143), which was produced by a fragment of DNA encoded in pKSD300 (McDaniel et al (III) 1987), produces a PspA fragment of 27 kDa (apparent molecular weight 43 kDa). This fragment is approximately 40% the size of the native 65 kDa (84 kDa apparent size) protein.

The expected molecular size is based on the deduced amino acid sequence and the apparent molecular size is based on migration in SDS-PAGE. The difference between expected and apparent molecular size is due to the conformation of the PspA fragment.

The proline and repeats/anchor regions (see FIG. 1) were deleted and the resulting protein was unable to attach to cell due to their absence. The unattached protein then may be isolated from culture supernatants, as described below.

By directing the insertion to different points in the pspA gene, different lengths of truncated, non-attached PspA protein derivatives can be produced, as seen in FIG. 7. The pneumococcal strain JY2008 was grown in 6 liters of a chemically defined medium (see Inf. Imm. 27:444) supplemented with 0.10% choline chloride, 0.075% L-cysteine hydrochloride and 0.25% $NaHCO_3$. The supernatant fluid of the mid-log phase culture of JY2008 was harvested using a 0.22 μm membrane tangential flow filter and concentrated 60 fold.

Introduction of the plasmid pKSD300 into the unmodified D39 strain similarly yielded the 43 kD truncated PspA protein. Introduction of the plasmid pKSD300 into the type 3 *S. pneumoniae* strain WU2 (PspA protein approximately 92 kD) yielded, upon growth of the organism, a non-attached truncated PspA protein of approximately 46 kD molecule size.

Example 2

This Example illustrates the purification of PspA.

The concentrated supernatant fluid, produced as described in Example 1, was washed in 0.1M PBS, pH 7.2, and ultracentrifuged at 196,000×g. The supernatant fluid was diluted 1:5 in 20 mM L-histidine buffer-NaCl, the pH adjusted to 6.0 and the injected into a DEAE-fibered Isonet-D2 an ion exchange column.

A stepwise NaCl gradient from 80 mM to 2M was applied to the column and PspA-containing fractions (0.32 to 0.64M ionic strength) were pooled and separated on an SDS-polyacrylamide gel. The proteins on a representative section of the gel were stained with Comassie Blue R-250 to identify PspA. The fraction containing PspA was excised from the remainder of the SDS-gel and electroeluted from the excised gel. The eluted protein was precipitated in a 50:50 methanol:acetone solvent and resuspended in PBS. Purity of product was confirmed by silver staining and Western Immunoblotting with mAb Xi126 (IgG 2b, k, see McDaniel et al (I), supra).

Example 3

This Example illustrates the isolation of PspA from the periplasmic space of *Escherichia coli*.

Isolation from the periplasmic space of *E. coli* was accomplished by standard techniques. *E. coli* strain JY4306 (which produces the 43 kDa N-terminal fragment of PspA, the amino acid sequence of which is shown in FIGS. 3A–C (SEQ ID NO: 2). This strain was deposited with ATCC on Jan. 31, 1991 under accession number 68522) was washed in buffered saline, incubated in 20% sucrose, 10 mM EDTA, 25 mM Tris pH 7.7 for 10 minutes at 0° C. The cells then were spun at 400×g for 10 minutes at 0° C. All supernatant was removed from the pellet and the pellet was resuspended rapidly in about 100 volumes of 4° C. water. After 10 minutes the suspension was centrifuged at 4,000×g for 10 minutes at 4° C. The pellet was discarded and the supernatant, which contained the PspA was saved. Concentration of the supernatant was by standard procedures such as concentration against solid sucrose or ultrafiltration. Purification of the protein isolated from *E. coli* proceeded by the same chromatography techniques used for the isolated of the 43 kDa (truncated) PspA from the media of growing pneumococci.

Example 4

This Example illustrates the immunogenic properties of the PspA protein.

Sixteen 7-week old CBA/N mice carrying the Xid mutation (Jackson Laboratories, Bar Harbor, Me.) were bled via the periorbital sinus to establish pre-exposure levels of antibody to PspA. Purified PspA, prepared as described in Example 2, was emulsified in complete Freund's adjuvant and injected subcutaneously into the inguinal and axillary regions, delivering approximately 5 μg of protein per mouse. Fourteen days later, the mice were injected intraperitoneally with 5 μg of PspA, prepared as described in Example 2. Control mice were immunized via the same routes with sterile SDS buffer. Seven days after the last immunization, all mice were bled via the periorbital sinus and were challenged intravenously with 300 CFU of the type 3 strain WU2, grown as described in Example 1.

Preimmunization and prechallenge sera were analyzed by Western immunoblots to establish baseline and postimmunization response to the truncated protein. The PspA of strain WU2 was electrophoresed and transferred to nitrocellulose membranes. The membranes were separated into strips and probed with the appropriate mouse antisera at a 1:50 dilution for 2 hours, incubated with biotinylated goat anti-mouse immunoglobulin for 1 hr, washed and incubated with Strepavidin-conjugated phosphatase. The membranes were developed with 5-bromo-4-chloro-3-indoyl phosphate toludine salt with 0.01% into blue tetrazolium.

Of the eight CBA/N mice immunized with the purified fragment of PspA, all were still alive 14 days after challenge with strain WU2 and none showed any signs of illness following challenge. Of the eight mice immunized with buffer controls, six were dead by two days post challenge, while the two remaining control mice appeared very sick, with ruffled fur, arched back and decreased movement, two to three days following challenge but survived. Chi-square analysis indicated that there was a significant difference ($P<0.003$) in survival between the immunized and control groups.

Preimmunization and prechallenge sera were analyzed by Western immunoblotting. None of the preimmunization sera contained antibody to truncated PspA. Postimmunization sera from eight of eight mice contained detectable antibodies to PspA, and six mice had very strong anti-PspA reactions. When the challenge strain WU2 was probed with the antisera, all the immunized mice had antibodies that were highly cross-reactive with the WU2 PspA epitopes. No control mice developed antibodies to PspA.

The immunization data is summarized in the following Table III:

TABLE III

| Immunogen | Detection of Antibody to PspA | Alive at 2 days post challenge | Alive at 14 days post challenge |
|---|---|---|---|
| Isolated PspA (Example 2) | 8/8 | 8/8 | 8/8 |
| Sterile SDS (control) | 0/8 | 2/8 | 2/8 |

As may be seen from the data in Table III, immunization with two 5 μg doses of the purified PspA molecule elicited protection against fatal infection of CBA/N mice and elicited antibodies reactive with the PspA of the challenge strain.

Example 5

This Example illustrates sequencing of the PspA protein.

Purified PspA, prepared as described in Example 2, was electrophoresed through 9% resolving gels containing recrystallized SDS with the Laemmli buffer system (Nature 227:680). The gels were soaked twice in a 10 mM 3-(cyclohexylamino)-1-propanesulfonic acid, pH 11.0, containing 10% methanol for 10 minutes. A polyvinylidene difluoride membrane (PVDF) was wetted completely for several seconds in 100% methanol, then washed in CAPS buffer for 10 min. PspA was electrotransferred to the PVDF membrane in CAPS buffer at 0.5 A for 1 hr. After transfer, the membrane was washed two times in deionized water for 5 min, and stained with 0.1% Coomassie Blue R-250 in 50% methanol for 20 minutes. The section of the membrane containing PspA was excised and destained in 40% methanol and 10% acetic acid for 5 min. The membrane was cut into small segments and stored in sterile Eppendorf tubes until sequencing.

The isolated PspA was sequenced directly from the PVDF membranes. FIG. 2 (SEQ ID NO: 3) depicts the N-terminal 45 residue amino acid sequence and FIG. 5 depicts the amino acid sequence for the whole alpha-helical region. The DNA sequence of the whole pspA gene and the deduced amino acid sequence for the PspA protein are shown in FIGS. 3A–C (SEQ ID NO: 1).

Example 6

This Example illustrates the use of the pspA 5'-sequence and/or the PspA N-terminal region to serve as an expression and leader sequence for expressing and/or excreting/secreting heterologous proteins from *S. pneumoniae* and *E. coli*. In this Example, there is described the expression of the N-terminal of the PspA protein fused to the B-subunit of cholera toxin (CTB) through a genetic fusion and the excretion of the fused protein from pneumococci and its secretion into the periplasmic space of *E. coli*.

A fusion protein consisting of CTB and the N-terminal half of PspA was constructed and expressed in *E. coli*. The HindIII/DraI pspA gene fragment used contained all the pspA transcription and translation initiation signals and the PspA signal peptide leader sequence for transport across the cell membrane. The mature PspA encoded by this fragment is predicted to be a product of 29 kDa (observed molecular weight of 42 kDa), encompassing more than 90% of the α-helical coiled-coil domain. The CTB fragment used lacked transcription and translation initiation signals. Expression from pspA promoter through pspA and then in-frame translational readthrough into the CTB-encoding gene ctxB resulted in production of a 12 kDa CTB product fused to the upstream PspA product. The PspA-CTB fusion protein was stably expressed in both high and low copy number plasmids (pUC18, more than 100 copies/cell; pJY4163, about 15 to 30 copies/cell) in *E. coli*.

The fusion products were of the expected size (about 54 kDa) and reacted with antibody to both PspA and CTB. That the CTB product retained its functionality was demonstrated by the ability of the fusion protein to bind ganglioside $G_{M1}$, a property of CTB.

The high level of expression of the fusion product apparently resulted in a reduced rate of processing and/or conformational changes that prevented the protein from being completely transported to the periplasm. However, in the lower copy number construct, about 60% of the fusion protein was localized in the periplasm, where large quantities were readily released from *E. coli* by osmotic shock.

In addition to expression in *E. coli*, the fusion protein also was expressed in *S. pneumoniae* by transformation of the low copy number construct into the avirulent *S. pneumoniae* Rx1 to generate an insertion-duplication mutant. In this way, the gene encoding the fusion protein was integrated into the *S. pneumoniae* chromosome, from which it was stably expressed. As in the case of Example 1, the truncated PspA molecule lacking the attachment/anchor region, this time in the form of the PspA-CTB fusion protein, was excreted into the culture supernatant. The fusion protein product was of the expected molecular size (54 kDa), reacted with antibody to PspA and CTB, and bound $G_{M1}$.

Example 7

This Example illustrates the use of PspA attachment or anchor region to permit expression of heterologous proteins on the surface of *S. pneumoniae* or other bacteria in which the attachment/anchor sequence is functional in particular the expression of a PspA-CTB (cholera toxin B subunit) fusion expressed on the surface of pneumococci.

The N-terminal encoding region of PspA, including its transcription and translation initiation signals and its signal peptide leader sequence, is linked via a translationally in-frame genetic fusion to the CTB-encoding ctxB fragment that lacks transcription and translation initiation and termination signals. This sequence is followed in-frame by the PspA attachment/anchor domain, including part or all of the proline, repeat and C-terminal domains. The resulting fusion protein is directed to the outside of the cell via the PspA leader sequence, which is cleaned following transport across the membrane, and then attached to cell by the PspA attachment/anchor sequence. The heterologous protein, located between the two PspA fragments is expressed on the outside surface of the membrane and, in *S. pneumoniae*, on the surface of the cell.

Example 8

This Example illustrates the expression of truncated and full length PspA by the *Mycobacterium tuberculosis* strain Bacille Calmette-Guerin (BCG).

BCG was chromosomally modified to incorporate the pspA gene coding for the truncated PspA protein. The 43 kDa truncated PspA protein was expressed from the modified BCG to approximately 15% of total BCG protein. This result was achieved with an expression vector construct carrying the pspA gene segment encoding the 43 kDa region without its 5'-secretion signal. Expression was only about 1% of BCG protein when the PspA or mycobacterial signal sequences were included. In either case, a significant portion of the expressed PspA was excreted into the medium.

Expression of the 43 kDa PspA protein in a fusion with the mycobacterial lipoprotein signal sequence resulted in the expression of the recombinant PspA in the membrane fraction of BCG.

This latter result suggested that the fusion of the lipoprotein signal sequence resulted in acylation of the recombinant PspA. Fluorescent activated cell sorting with fluorochrome-conjugated monoclonal antibodies to PspA demonstrated expression of PspA on the surface of these bacteria.

Example 9

This Example illustrates the close homology of portions of the pspA gene among different strains of pneumococci and the potential that such homology may be useful for molecular (DNA) approaches to detect pneumococci in tissues, body fluids and/or secretions and to identify pneumococci grown from patient samples.

Three DNA probes were employed, namely full length pspA, JY4323 (N-terminal HindIII to C-terminal KpnI), the N-terminal half of pspA, JY4306 (N-terminal HindIII to DraI at position 996 (see FIGS. 3A–C (SEQ ID NO: 1)) and most of the proline and repeat regions, JY4262 (BclI at position 1221 to BstNI at position 1832). Under stringency conditions requiring 95% identity, probes JY4323 and JY4262 reacted with cells of over 200 independent isolates of S. pneumoniae by Southern blot.

When the chromosomal DNA was cut with HindIII, there generally was observed that each of these probes detected two discrete bands whose exact size was dependent on the strain examined. In Rx1 pneumococci, the two bands were 4.0 and 9.1 kb. The 4.0 kb band corresponded to pspA and was altered or absent in pspA mutants. The other band shares some homology with the coding regions for both the N-terminal and C-terminal halves of PspA but is not affected by pspA mutations. The JY4323 and JY4262 probes failed to react with another gram positive bacterium, Streptococcus pyogenes, and a gram negative bacterium, Salmonella typhimurium. The N-terminal probe, JY4306, recognized about one-third of the strains of pneumococci tested.

These results indicate that a sequence included in the proline/repeat region is shared by all strains of pneumococci and apparently not by other bacterial species. Sequences in the N-terminal half of the molecule appear to be more variable.

Example 10

This Example illustrates the detection and determination of the location of epitopes in the α-helical N-terminal region of PspA.

Monoclonal antibodies protective against pneumococcal infection in a mouse model, denoted by an asterisk in FIGS. 5 (SEQ ID NO: 4), 6 and 7, were used to determine the location of epitopes for each antibody in the α-helical N-terminal region of PspA. The sites were mapped to fragments of PspA. The results are illustrated in FIGS. 5 to 7, with FIG. 5 (SEQ ID NO: 4) showing the deduced amino acid sequence for the N-terminal region of PspA and the general location of epitopes recognized by monoclonal antibodies, FIG. 6 showing antibody reactivity with PspA fragments produced by various pspA gene segments, and FIG. 7 showing the mapped location of epitopes in the PspA fragments produced by the different pspA gene segments.

Numbers 138, 193 and 261 in FIG. 5 (SEQ ID NO: 4) indicate break positions in the PspA fragments used to map the location of epitopes detected by monoclonal antibodies Xi1526, Xi126, XiR35, XiR38, XiR1224, XiR16, Xi64, XiR278, Xi1325 and Xi1323. The asterisk (*) after some of the antibodies denotes those which are able to protect against fatal pneumococcal infection with strain WU2 pneumococci.

In addition, the vertical lines to the right of the Figure indicate those areas predicted to have coiled-coil α-helical structure. The divisions to the left of the Figure indicate the mapped location of the epitopes for each antibody.

SUMMARY OF DISCLOSURE

In summary of this disclosure, the present invention relates to a truncated PspA molecule capable of eliciting an immunoprotective response and hence containing the protective epitopes of PspA protein. Modifications are possible within the scope of this invention.

SEQUENCE LISTINGS

Submitted with this application are Sequence Listings, identified as follows:

(a) SEQ ID No: 1 shows the nucleotide sequence and derived amino acid sequence for the HindIII-KpnI fragment containing the complete pspA gene, as shown in FIG. 3.

(b) SEQ ID No: 2 shows the derived amino acid sequence for the PspA protein, as shown in FIG. 3.

(c) SEQ ID No: 3 shows the N-terminal amino acid sequence of PspA, as shown in FIG. 2.

(d) SEQ ID No: 4 shows the derived amino acid sequence for the N-terminal region of PspA as shown in FIG. 5.

(e) SEQ ID No: 5 shows the nucleotide sequence for primer LSM1.

(f) SEQ ID No: 6 shows the nucleotide sequence for primer LSM2.

---

What we claim is:

1. A recombinant DNA molecule comprising a nucleotide sequence coding for a truncated form of whole pneumococcal surface protein (PspA), wherein said truncated form of the PspA is linked by a translationally in frame genetic fusion to a ctxB gene, and said truncated form of the PspA contains immunoprotective epitopes and up to 90% of the whole PspA from which the cell membrane anchor region is absent, wherein said whole PspA comprises the sequence as set forth in SEQ ID No. 2.

2. A mutated strain of *Streptococcus pneumoniae* comprising the recombinant DNA molecule of claim 1.

3. Plasmid pJY4163.

4. A method for production of a fusion protein which comprises:

transforming a bacterium selected from the group consisting of *Streptococcus pneumoniae* and *Escherichia coli* with the recombinant DNA molecule of claim 1, growing the transformed bacterium to express a fusion protein comprising the truncated form of the PspA and B-subunit of cholera toxin (CTB).

5. The method of claim 4, wherein said bacterium is a strain of *Streptococcus pneumoniae.*

6. The method of claim 4, wherein said bacterium is a strain of *Escherichia coli.*

7. The method of claim 4, wherein said fusion protein is isolated by adsorption to a $G_{M1}$ affinity column, from which said fusion protein is eluted.

* * * * *

UNITED STATES PATENT AND TRADEMARK OFFICE
CERTIFICATE OF CORRECTION

PATENT NO. : 5,753,463
DATED : May 19, 1998
INVENTOR(S) : Briles et al.

It is certified that error appears in the above-identified patent and that said Letters Patent is hereby corrected as shown below:

In the Drawings delete Figure 3 and insert substitute Figure 3 (enclosed).

Signed and Sealed this

Twenty-sixth Day of February, 2002

*Attest:*

JAMES E. ROGAN
*Attesting Officer*   *Director of the United States Patent and Trademark Office*

FIG. 3A

PspA - sequence -> 1-phase Translation
and derived amino acid
DNA \ sequence    2086 b.p.    AAGCTTATGATA ... TCTTTAGGTACC    linear

```
  1 /        1                    11                    21                    31                    41                    51
AAG CTT ATG ATA TAG AAA TTT GTA ACA AAA ATG TAT AAA ACA CTT GAC AAA TAT TTA
                                                                    └─CONSENSUS-35─┘

61 /       21
CGG AGG AGG CTT AAT ATA AGT ATA GTC AAA TGA CTA TCA GAA AAG AGG TAA
                                                        └──SD──┘     ↑
                                                              TRANSLATION
                                                              START AT ATG met 121 /       41  → START
ATT TAG ATG AAT AAG AAA AAA ATT TTA ACA AGT CTA GCC AGG GTC GCT ATC TTA GGG
         met asn lys lys lys lys ile leu thr ser leu ala ser val ala ile leu gly
         └─ -10 ─┘          ┌────────────── LEADER ──────────────

181 /       61
GCT GCT TTT GTT GCG TCT CAG CCT GTT GTA AGA GCA GAA GAT GCC AGC GTC GCT ATC TTA GGG
ala ala phe val ala ser gln pro val val arg ala glu asp ala ser val ala ile leu gly
                                                        ──────── LEADER
                                                        SEQUENCE IS
                                                        CLEAVED.

241 /       81
GAG TCT AAA GCT GAG AAA AAG GAC TAT GAT GCA AAG GAT CTA GCC AGG GTC GCT ATC TTA GGG
glu ser lys ala glu lys lys asp tyr asp ala lys asp leu ala ser pro val ala ser
                                                                         ↑
                                                                    "NATURE" PspA
                                                                    BEGINS WITH
                                                                    glu.

301 /      101
CAG TCT AAA GCT GAG AAA AAG GAC TAT GAT GCA AAG GAT CTA GCC AGG GTC GCT ATC TTA GGG
gln ser lys ala glu lys lys asp tyr asp ala lys asp leu ala lys asn ala lys lys 361 /      121                                              131
GCA GTA GAA GAT GCT CAA AAG CTT ACA GAT GAT GCA AAA GCT CAG AAA TAT GAC
ala val glu asp ala gln lys leu asp asp ala lys lys gln lys tyr asp 421 /      141                                                  151
GAG GAT CAG AAG AAA ACT GAG GAA AAA GCG CTA GAA CTA GCA CTA AAG GAA GAG ATG
glu asp gln lys lys thr glu glu lys ala leu glu leu ala lys lys glu glu met 451 /      151
GAT AAG GCA GTG GCA GCA GTT CAA CAA GCG TAT CTA GCC TAT CAA CAA GCT ACA GAC AAA
asp lys ala val ala ala val gln gln ala tyr leu ala tyr gln gln ala thr asp lys
```

☐ = SIGNALS FOR
TRANSCRIPTION/
TRANSLATION.

FIG. 3B

```
481   GCC GCA AAA GAC GCA GCA GAT AAG ATG ATA GAT CAA GCT AAG AAA CGC GAA GAG GCA
      ala ala lys asp ala ala asp lys met ile asp ala lys lys arg glu glu ala
541 / 181                                       511 / 171
AAA ACT AAA TTT AAT ACT GTT CGA GCA GCA ATG GTA CTT CCT GAG CCA CAG TTG GCT GAG
lys thr lys phe asn thr val arg ala ala met val pro glu pro gln leu ala glu
601 / 201                                       631 / 211
ACT AAG AAA AAA TCA GAA GAA GCT AAA AAA GCA CCA GAA CTT ACT AAA AAA CTA GAA
thr lys lys lys ser glu glu ala lys lys ala pro glu leu thr lys lys leu glu
661 / 221                                       691 / 231
GAA GCT AAA GCA AAA TTA GAA GAG GCT GAG AAA CAA AAA CTT GAA AAA CAA AAA GTG
glu ala lys ala lys leu glu glu ala glu lys gln lys leu glu lys gln lys val
721 / 241                                       751 / 251
GAT GCT GAA GTC GCT CCT CAA GCT AAA ATC GCT GAA AAT GCC CAT AGA
asp ala glu val ala pro gln ala lys ile ala glu asn ala his arg
781 / 261                                       811 / 271
CTA GAA CAA GAG CTC AAA GAG ATT GAT CAG TCT GAA TCA GAT GCT GAA GGT
leu glu gln glu leu lys glu ile asp gln ser glu ser asp ala glu gly
841 / 281                                       871 / 291
TTC CCT CCT CTT CAA TCT AAA TTG GAT CCC AAA AAA GCT AAA TCA AAA CTT GAA
phe arg ala pro leu gln ser lys leu asp pro lys lys ala lys ser lys leu glu
901 / 301                                       931 / 311
GAG TTA AGT AAG ATT GAT GAG TTA GAC GCT GAA ATT GCA AAA CTT GAA CAA CTT
glu leu ser lys ile asp glu leu asp ala glu ile ala lys leu glu gln leu
961 / 321                                       991 / 331
AAA GCT GAA GAA AAC AAT AAT GTA GAA GAC TAC TTT AAA GAA GGT TTA GAG AAA ACT
lys ala glu glu asn asn asn val glu asp tyr phe lys glu gly leu glu lys thr
lys ala ala glu glu asn asn asn val glu asp tyr
```

FIRST 45 aa, BEGINNING WITH glu, ARE SAME AS FOUND BY aa SEQUENCING (TALKINGTON ETC.)

α-HELICAL CHARGED DOMAIN

FIG. 3C

```
1021 /  341
ATT GCT AAA AAA GCT GAA TTA GAA AAA ACT GAA GCT GAC CTT AAG AAA GCA GTT AAT
ile ala lys lys ala glu leu glu lys thr glu ala asp leu lys lys ala val asn
1081 /  361
GAG CCA GAA AAA CCA GCT CCA GAA ACT CCA GCC GAA GCA CCA GCT GAA CAA
glu pro glu lys pro ala pro glu thr pro ala pro ala pro ala glu gln
1141 /  381
CCA AAA CCA GCG CCG CCT CAA CCA CCC AAA GAG AAG CCA CCA GCT GAA
pro lys pro ala pro pro gln pro pro lys glu lys pro pro ala glu
1201 /  401
CAA CCA AAA ACA GAT CAA CAA GCT GAA GAC TAT GCT CGT AGA TCA
gln pro lys thr asp gln gln ala glu asp tyr ala arg arg ser
1261 /  421
GAA GAA TAT CGC TTG ACT CAA CAG CCA CCG AAA GCT GAA CCA GCT CCT
glu glu tyr arg leu thr gln gln pro pro lys ala glu pro ala pro  PROLINE-RICH DOMAIN
1321 /  441                                                       PROLINES
GCA CCA AAA GGC TGG AAA CAA GGT ATG TGG TAC TTC TAC AAT ACT GAT GGT
ala pro lys gly trp lys gln gly met trp tyr phe tyr asn thr asp gly
1381 /  461
TCA ATG GCG ACA GGA TGG CTC CAA AAC AAC GGT TAC CTC AAT AGC AGC GGT
ser met ala thr gly trp leu gln asn asn gly tyr leu asn ser ser gly
1441 /  481
GCT ATG GCT ACA GGT TGG GCT AAA GTC AAG AAC GGT TCA TGG TAT TAC CTC AAC GCT AAC GGT
ala met ala thr gly trp ala lys val asn gly ser trp tyr tyr leu asn ala asn gly
1501 /  501
GCT ATG GCA ACA GGT TGG GCT AAA GTC AAG AAC GGT TCA TGG TAT TAC CTC AAC GCT AAC GGT
ala met ala thr gly trp ala lys val asn gly ser trp tyr tyr leu asn ala asn gly
1561 /  521
GCT ATG GCT ACA GGT TGG CTC CAA TAC AAC AAC GGT TCA TGG TAT TAC CTC AAC AAC GGC
ala met ala thr gly trp leu gln tyr asn asn gly ser trp tyr tyr leu asn asn gly
```

FIG. 3D

```
1621 /  541
GCT ATG GCA ACA GGT TGG GCT AAA GTC AAC GCT AAT GGT
ala met ala thr gly trp ala lys val asn ala asn gly
                                      1651 /  551
GCT ATG GCT ACA GGT TGG TCA TAC TAC TAC CTC AAC GCT
ala met ala thr gly trp ser tyr tyr tyr leu asn ala
1681 /  561                                          
GCT ATG GCT ACA GGT TGG CTC CAA TAC TAC TAC CTC AAC GCT
ala met ala thr gly trp leu gln tyr tyr tyr leu asn gly
                                      1711 /  571
GCT ATG GCT ACA GGT TGG CAA TAC TAC TAC CTC AAC GCT
ala met ala thr gly trp gln tyr tyr tyr leu asn gly
1741 /  581
GCT ATG GCT ACA GGT AAA GTC AAC GGT TCA TGG TAC TAC TAC CTC AAC AAT GGT
ala met ala thr gly lys val asn gly ser trp tyr tyr tyr leu asn asn gly
                                      1771 /  591
GCT ATG ACA GGT TGG AAA GTC GGT ACC TGG TAC TAC TAT CTT GAA GCA TCA GGT
ala met thr gly trp lys val gly thr trp tyr tyr tyr leu glu ala ser gly
1801 /  601
GCT ATG GCT ACA GGT TGG GTC AAA GAT GCA AAC TGG TAC TAC TAT CTT GAA GCA TCA GGT
ala met ala thr gly trp val lys asp ala asn trp tyr tyr tyr leu glu ala ser gly
                                      1831 /  611
GCT ATG AAA GCA AGC CAA TGG TTC AAA TCA GAT AAA TGG TAC TAC TAT GTC AAT TTA
ala met lys ala ser gln trp phe lys ser asp lys trp tyr tyr tyr val asn leu
1861 /  621
GCT ATG AAA GCA AGC CAA TGG TTC AAA GTA TCA GAT AAA TGG TAC TAC TAT GTC AAT TTA
ala met lys ala ser gln trp phe lys val ser asp lys trp tyr tyr tyr val asn leu
1921 /  641
GCT GCC CTT GCA AAC ACA ACT GTA GAT GGC TAT AAA GTC GTC AAT GCC AAT GGT GAA TGG
ala ala leu ala asn thr thr val asp gly tyr lys val val asn ala asn gly glu trp  ] TAIL
1981 /  661
GTT TAA GCC GAT TAA ATT AAA GCA TCT TAA GAA CAT TTG ACA CAT TTG TGA AAC AAA
val OCH ala asp OCH ile lys ala cys OCH glu his leu thr phe OCH phe OPA asn lys
2041 /  681
GAT AAG GTT CGA TTG AAT AGA TTT ATG TTC GTA TTC TTT AGG TAC
asp lys val arg leu asn arg phe met phe val phe phe arg tyr
                              2071 /  691
                      TRANSLATION STOP (END) IS AT TAA OCH
```

REPEAT DOMAIN